US005670486A

United States Patent [19]

Mynderse et al.

[11] Patent Number: 5,670,486
[45] Date of Patent: Sep. 23, 1997

[54] A83543 COMPOUNDS AND PROCESS FOR PRODUCTION THEREOF

[75] Inventors: Jon S. Mynderse, Indianapolis, Ind.; James A. Mabe, Hendersonville, N.C.; Jan R. Turner, Carmel, Ind.; Mary L. B. Huber, Danville, Ind.; Mary C. Broughton, Indianapolis, Ind.; Walter M. Nakatsukasa, Seattle, Wash.; Lawrence Creemer; Herbert A. Kirst, both of Indianapolis, Ind.; James W. Martin, Coatesville, Ind.

[73] Assignee: DowElanco, Indianapolis, Ind.

[21] Appl. No.: 483,440

[22] Filed: Jun. 7, 1995

Related U.S. Application Data

[62] Division of Ser. No. 385,497, Feb. 8, 1995, which is a division of Ser. No. 30,522, Mar. 12, 1993, abandoned.

[51] Int. Cl.⁶ .......................... A61K 31/71; C07H 17/04; C12P 19/62
[52] U.S. Cl. .............. 514/28; 424/DIG. 8; 424/DIG. 10; 536/41; 536/16.8; 536/7.1; 536/7.5
[58] Field of Search .............. 514/28; 424/DIG. 8, 424/DIG. 10; 536/4.1, 16.8, 7.1, 7.5

[56] References Cited

U.S. PATENT DOCUMENTS

| | | | |
|---|---|---|---|
| 2,881,162 | 4/1959 | Walasek | 260/210 |
| 3,725,385 | 4/1973 | Freiberg | 260/210 AB |
| 4,148,883 | 4/1979 | Celmer et al. | 424/122 |
| 4,206,206 | 6/1980 | Mori et al. | 435/822 |
| 4,213,966 | 7/1980 | Liu et al. | 424/123 |
| 4,224,314 | 9/1980 | Celmer et al. | 424/122 |
| 4,251,506 | 2/1981 | Laby | 424/19 |
| 4,251,511 | 2/1981 | Whaley et al. | 424/122 |
| 4,273,920 | 6/1981 | Nevin | 528/361 |
| 4,293,651 | 10/1981 | Whaley et al. | 435/822 |
| 4,321,329 | 3/1982 | Whaley et al. | 435/822 |
| 4,366,308 | 12/1982 | Soma et al. | 536/128 |
| 4,421,760 | 12/1983 | Box | 424/274 |
| 4,448,970 | 5/1984 | Magerlein | 548/311.7 |
| 4,482,707 | 11/1984 | Sakakibara et al. | 536/16.8 |
| 4,501,752 | 2/1985 | Yokoi et al. | 514/414 |
| 4,508,647 | 4/1985 | Hatori et al. | 260/239.3 T |
| 4,514,562 | 4/1985 | Toscaro | 336/7.4 |
| 4,515,942 | 5/1985 | Iwasaki et al. | 435/822 |
| 4,530,835 | 7/1985 | Bunge et al. | 424/117 |
| 4,560,509 | 12/1985 | Johnson et al. | 260/239.3 P |
| 4,568,740 | 2/1986 | Oppici et al. | 536/7.5 |
| 4,764,602 | 8/1988 | Kumagai et al. | 536/7.1 |
| 4,831,016 | 5/1989 | Mrozik et al. | 514/30 |
| 5,003,056 | 3/1991 | Nishikiori et al. | 536/71 |
| 5,028,536 | 7/1991 | Golik et al. | 435/101 |
| 5,202,242 | 4/1993 | Mynderse et al. | 435/76 |
| 5,227,295 | 7/1993 | Baker et al. | 435/76 |
| 5,362,634 | 11/1994 | Boeck et al. | 435/76 |

FOREIGN PATENT DOCUMENTS

| | | |
|---|---|---|
| 0 214 731 A3 | 3/1987 | European Pat. Off. . |
| 375316 | 12/1989 | European Pat. Off. . |
| 62-226925 | 10/1987 | Japan . |
| 2 059 767 | 9/1979 | United Kingdom . |
| WOA91 06552 | 5/1991 | WIPO . |
| WO93/09126 | 5/1993 | WIPO . |

OTHER PUBLICATIONS

Whaley et al., Tetrahedron Letters (1980), 21:3659.
Snyder et al., J. Am. Chem. Soc. (1984), 106:787.
Celmer et al., J. Chem. Soc., (1980) 102:4203.
Ikeda et al., (1985) J. Antibiotic, 38:436.
Umezawa (1980),Supplement to Index of Antibiotics from Actinomycetes, Journal of Antibiotics, 33(3):15–26.
Umezawa, Institute of Microbial Chemistry, Tokyo, Index of Antibiotics from Actinomycetes, vol. II (1967).
Sakano et al.(1980), J. Antibiot. (Tokyo), 33(7):683–689.
Brown et al. (1986), J. Liq. Chromatography, 9(4):831–844.
Chen et al. (1981), ACTA Microbiol. Sin., 21(2):192–196 (Biosis abstract).
Drioli, (1986), Separation, Recovery and Purification in Biotechnology, 52–66.
Kubo et al. (1985), Analytical Letters, 18(B3):245–260.
Brode et al. (1986), Arzneim–Forsch, 36(3):437–442.
Julien et al. (1988), Clin. Chem., 34(5):966–969.
Chemical Abstracts, vol. 87, No. 24, issued Dec. 1977, R. Datta et al., "Concentration of antibiotics by reverse osmosis," see p. 310, see the abstract No. 189423a, Biotechnol. Bioeng. 1977, vol. 19, No. 10, pp. 1419–1429.
Cram et al. (1964), Organic Chemistry, 2nd Ed., p. 204.
Journal of American Chemical Society, (1992), vol. 114, No. 6, pp. 2260–2262 Evans, et al. "Asymmetric Synthesis of the Macrolide (+)–A83543A (Lepicidin) Aglycone," see the whole document.
Chemical Abstracts (1991), vol. 114, No. 80066m, Boeck et al.
Biosis Abstract 90:127301 Mertz et al., "Int. J. Syst. Bact." 40(1) 1990 34–39.
ACS Symposium Series, Synthesis and Chemistry of Agrochemicals III, vol. 504, 1992, pp. 214–225, Kirst, et al., "Discovery, Isolation, and Structure Elucidation of a Family of Structurally Unique, Fermentation–Derived Tetracyclic Macrolides", See abstract. See p. 216, paragraph 2; p. 217, paragraph 1.
Jacobson, G.K., "Mutations" Chapter 5b of *Biotechnology* vol. 1, H.–J. Rehm and G. Reed, eds. (1981).

(List continued on next page.)

*Primary Examiner*—John W. Rollins
*Assistant Examiner*—Francisco C. Prats
*Attorney, Agent, or Firm*—Andrea T. Borucki

[57] ABSTRACT

New A83543 components, including fermentation products A83543K, A83543O, A83543P, A83543U, A83543V, A83543W and A83543Y and N-demethyl derivatives, and salts thereof, are useful for the control of insects and mites. The pseudoaglycones of the new A83543 components are useful for the preparation of A83543 components. Methods are provided for making the new A83543 components by culturing of *Saccharopolyspora spinosa* NRRL 18395, NRRL 18537, NRRL 18538, or NRRL 18539, or NRRL 18743 or NRRL 18719 or NRRL 18823 in suitable culture medium. Insecticidal and ectoparasiticidal compositions containing new A83543 components are also provided.

2 Claims, 20 Drawing Sheets

OTHER PUBLICATIONS

Journal of the Chemical Society, (1964), London, GB; Birch et al.: "Studies in Relation to Biosynthesis. Part XXXV. Macrolide Antibiotics to Biosynthesis. Part XII. Methymycin", pp. 5274–5278.

Chemical Abstracts, (1979), vol. 90, No. 19, p. 591, col. 2—p. 592, col. 1, abstract No. 151957b, Columbus, Ohio; Inanaga et al.: "Synthesis of Methynolide", & Tennen Yuki Kagobutsu Toronkal Koen Yoshishu, 21st 1978, 324–30 (abstract).

Kirst et al., Tetrahedron Letters (1991), 32(37):4839–4842.

Omura and Tannaka (1984), Macrolide Antibiotics, Chapter 1.

Schulman and Ruby (1987), Antimicrobial Agents and Chemotherapy, 31(6):964–965.

Ito and Hirata (1972), Tetrahedron Letters, 12:1185–1188.

Aizawa et al., (1979), The Journal of Antibiotics, 32(3):193–196.

Jomon et al., (1972), The Journal of Antibiotics, 25(5):271–280.

Dybas and Babu (1988), Brighton Crop Protection Conference, 57–64.

Borchardt et al. (1979), Biochem. & Biophys. Res. Comm., 89(3):919–924.

Vedel et al., (1978), Biochem. & Biophys. Res. Comm., 85(1):371–376.

Pickett, J.A., (1988), Chemistry in Brittain, 137–142.

Omura, (1984), Macrolide Antibiotics, Chapter 13.

Fuller (1978), Biochemical Pharmacology, 27:1981–1983.

Jackson et al. (1988), Abstracts of the 1988 ICAAC, 26026.

Derwent Abstract 84–278337/45,SSSE Mar. 16, 1983.

Derwent Abstract 84–252941/41, SSSE Feb. 16, 1983.

Derwent Abstract 92: 144960k.

Derwent Abstract 11667c/07, KAKE May 31, 1978.

Derwent Abstract 92:211459u.

Derwent Abstract 88–095030/14, SSSE 00.00.86.

Derwent Abstract 85–245719/40, SSSE Feb. 1, 1984.

Derwent Abstract 54333S–BCD,Fuji, Feb. 17, 1969.

Catalogue of Bacteria and phages, ATCC, 7th Ed., 1989.

Kreuzman et al., J. Biological Chemistry (1988), 263 (30): 15626–15633.

Schulman et al., Journal of Antibiotics 38(11): 1494–98 (1985).

A83543 COMPOUNDS AND PROCESS FOR PRODUCTION THEREOF

This is a divisional of application Ser. No. 08/385,497 filed Feb. 8, 1995 which is a divisional of application Ser. No. 08/030,522 filed Mar. 12, 1993 and is now abandoned.

FIELD OF THE INVENTION

The invention relates to new components of fermentation product A83543.

BACKGROUND OF THE INVENTION

Target insects are rapidly developing resistance to the insecticides which are presently available. Resistance to insecticides in arthropods is widespread, with at least 400 species exhibiting resistance to one or more insecticides. The development of resistance to older insecticides, such as DDT, the carbamates, and the organophosphates, is well documented (see Brattsten, et al. (1986), *Science,* 231:1255). Resistance to synthetic insecticides has developed extremely rapidly, including the development of resistance to the newer pyrethroid insecticides (see Pickett (1988), *Chem. Britain,* 137). Therefore, new insecticides are in demand.

Fermentation product A83543, a family of related compounds produced by *Saccharopolyspora spinosa*, was recently discovered and was shown to exhibit excellent insecticidal activity. A83543 and its individual compounds are useful for the control of mites and insects, particularly Lepidoptera and Diptera species.

By "A83543 compounds" is meant components consisting of a 5,6,5-tricylic ring system, fused to a 12-membered macrocyclic lactone, a neutral sugar and an amino sugar (see Kirst et al. (1991), *Tetrahedron Letters,* 32:4839). The family of natural components of A83543 include a genus taught in EPO Application No. 0375316 and having the following general formula:

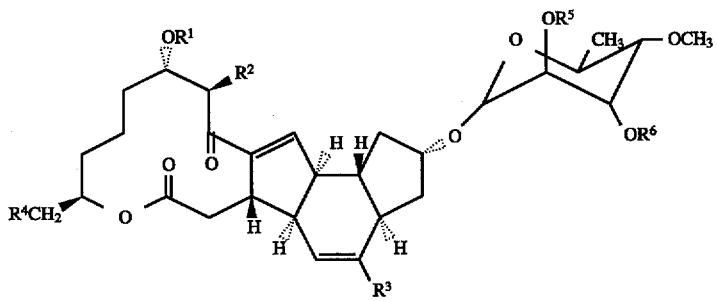

wherein $R^1$ is H or a group selected from

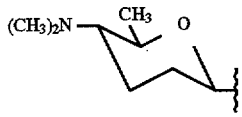 (a)

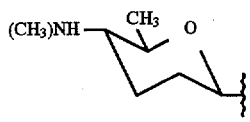 (b)

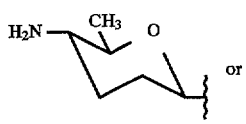 (c)

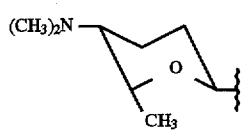 (d)

and $R^2$, $R^4$, $R^3$, $R^5$ and $R^6$ are hydrogen or methyl; or an acid addition salt thereof when $R^1$ is other than hydrogen.

The family of compounds from A83543 fermentation product has been shown to comprise individual components A83543A, A83543B, A83543C, A83543D, A83543E, A83543F, A83543G, A83543H and A83543J (see European Patent Publication No. 0 375 316); individual components A83543L, A83543M and A83543N (see copending U.S. patent application No. 07/790,287, filed Nov. 8, 1991); and individual components A83543Q, A83543R, A83543S and A83543T (see the copending United States Patent Application of Turner, Broughton, Huber and Mynderse, entitled "New A83543 Compounds and Processes for Production Thereof" (U.S. patent application Ser. No. 07/973,121), filed on Nov. 6, 1992). The structures of these individual components and pseudoaglycones derived therefrom are shown below.

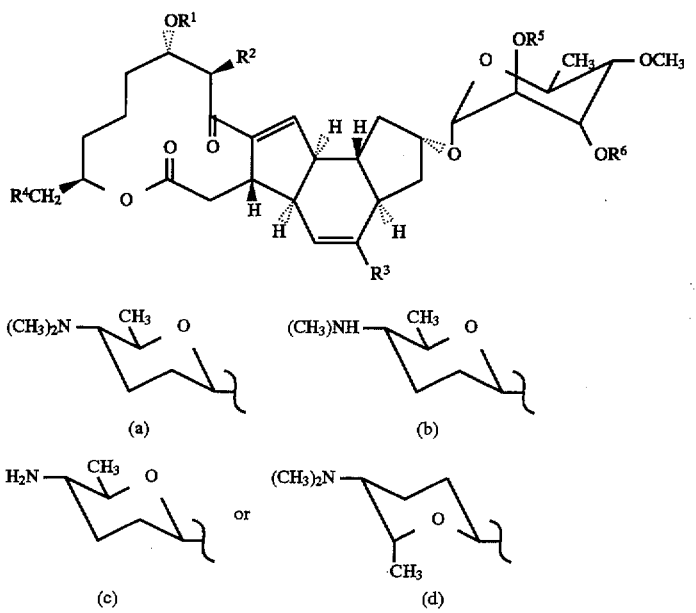

wherein $R^1$, $R^2$, $R^3$, $R^4$, $R^5$ and $R^6$ are for each component as follows:

| Structures of A83543 Components | | | | | | |
|---|---|---|---|---|---|---|
| Component | $R^1$ | $R^2$ | $R^3$ | $R^4$ | $R^5$ | $R^6$ |
| A | (a) | Me | H | Me | Me | Me |
| B | (b) | Me | H | Me | Me | Me |
| C | (c) | Me | H | Me | Me | Me |
| D | (a) | Me | Me | Me | Me | Me |
| E | (a) | Me | H | H | Me | Me |
| F | (a) | H | H | Me | Me | Me |
| G | (d) | Me | H | Me | Me | Me |
| H | (a) | Me | H | Me | H | Me |
| J | (a) | Me | H | Me | Me | H |
| L | (a) | Me | Me | Me | Me | H |
| M | (b) | Me | H | Me | Me | H |
| N | (b) | Me | Me | Me | Me | H |
| Q | (a) | Me | Me | Me | H | Me |
| R | (b) | Me | H | Me | H | Me |
| S | (a) | Me | H | H | H | Me |
| T | (a) | Me | H | Me | H | H |
| PsaA1 | H | Me | H | Me | Me | Me |
| PsaD1 | H | Me | Me | Me | Me | Me |
| PsaE1 | H | Me | H | H | Me | Me |
| PsaF1 | H | H | H | Me | Me | Me |
| PsaH1 | H | Me | H | Me | H | Me |
| PsaJ1 | H | Me | H | Me | Me | H |
| PsaL1 | H | Me | Me | Me | Me | H |
| PsaQ1 | H | Me | Me | Me | H | Me |
| PsaR1 | H | Me | H | Me | H | Me |
| PsaS1 | H | Me | H | H | H | Me |
| PsaT1 | H | Me | H | Me | H | H |

Sinefungin, an antibiotic of microbial origin, has been shown to inhibit specific S-adenosylmethionine-dependent methyltransferases. This compound is effective in inhibiting the following mammalian methyltransferases: norepinephrine N-methyltransferase, histamine N-methyltransferase and catechol O-methyltransferase (see Fuller and Nagarajan (1978), *Biochemical Pharmacology*, 27:1981). Sinefungin is also effective in inhibiting the S-adenosyl-methionine-dependent O-methyltransferase in avermectin-producing strains of *Streptomyces avermitilis* (see Schulman, et al. (1985), *J. Antibiotics*, 38:1494). More recently, sinefungin was reported effective in inhibiting an S-adenosylmethionine-dependent O-methyltransferase (macrocin O-methyltransferase) in *Streptomyces fradiae* (see Kreuzman, et al. (1988), *J. Biological Chemistry*, 263:15626). A method of using sinefungin to inhibit an O-methyltransferase in strains of *S. spinosa* is disclosed herein.

SUMMARY OF THE INVENTION

The present invention is directed to a new genus of the A83543 family of compounds, said genus including compounds of Formula 1

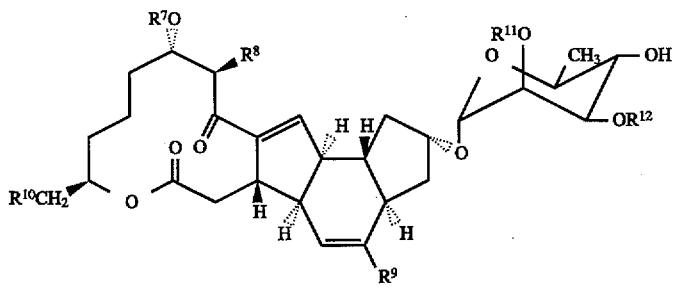
(1)

wherein $R^7$ is hydrogen or a group of formula

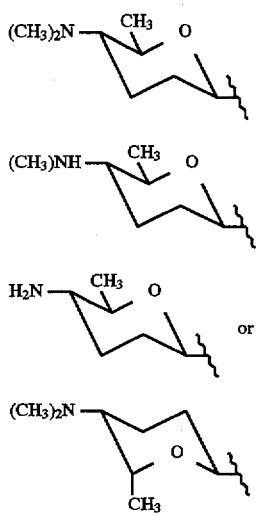

(a)

(b)

(c)

or (d)

$R^8$, $R^9$, $R^{10}$, $R^{11}$, and $R^{12}$ are independently hydrogen or methyl, provided that $R^{11}$ and $R^{12}$ are not concurrently hydrogen; or an acid addition salt thereof when $R^7$ is other than hydrogen.

In particular, this invention relates to new components of fermentation product A83543. The new components, termed Formula 2 compounds, have the following general formula:

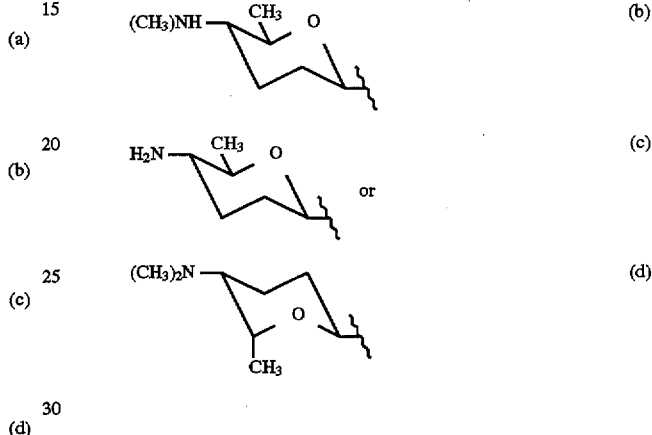

-continued (b)

(c)

or (d)

and $R^{14}$, $R^{15}$, $R^{16}$, $R^{17}$ and $R^{18}$ are independently hydrogen or methyl, provided that $R^{17}$ and $R^{18}$ are not concurrently hydrogen; or an acid addition salt thereof when $R^1$ is other than hydrogen.

Preferably, this invention relates to new A83543 components, Formula 2 components, designated A83543K, A83543O, A83543P, A83543U, A83543V, A83543W and A83543Y, wherein $R^{13}$, $R^{14}$, $R^{15}$, $R^{16}$, $R^{17}$ and $R^{18}$ are for each component as follows:

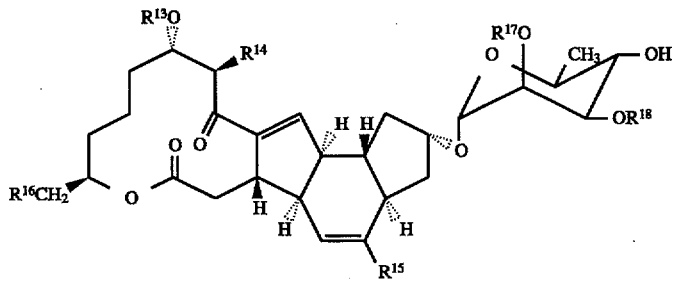
(2)

wherein $R^{13}$ is a group of formula

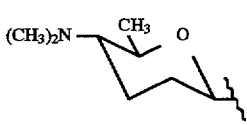

(a)

| Component | $R^{13}$ | $R^{14}$ | $R^{15}$ | $R^{16}$ | $R^{17}$ | $R^{18}$ |
|---|---|---|---|---|---|---|
| K | (a) | $CH_3$ | H | $CH_3$ | $CH_3$ | $CH_3$ |
| O | (a) | $CH_3$ | $CH_3$ | $CH_3$ | $CH_3$ | $CH_3$ |
| P | (a) | $CH_3$ | H | $CH_3$ | $CH_3$ | H |
| U | (a) | $CH_3$ | H | $CH_3$ | H | $CH_3$ |
| V | (a) | $CH_3$ | $CH_3$ | $CH_3$ | H | $CH_3$ |
| W | (a) | $CH_3$ | $CH_3$ | $CH_3$ | $CH_3$ | H |
| Y | (a) | $CH_3$ | H | H | $CH_3$ | $CH_3$ |

Another aspect of this invention is a process for producing a compound of Formula 1, which comprises culturing a strain of *S. spinosa*, selected from strains NRRL 18395 (A83543.1), NRRL 18537 (A83543.3), NRRL 18538 (A83543.4), NRRL 18539 (A83543.5), NRRL 18719 (A83543.6) and NRRL 18823 (A83543.9) or a Formula 1-producing mutant thereof, in a suitable culture medium, containing from about 50 μg/ml to about 200 μg/ml of sinefungin, under submerged aerobic conditions until a recoverable amount of a compound of Formula 1 is produced. The Formula 1 compound is extracted from the fermentation broth and from the mycelium with polar organic solvents. The compound may be further purified by techniques well known in the art, such as column chromatography.

A still further aspect of the present invention is a process for producing a compound of Formula 1 which comprises cultivating *S. spinosa* strain NRRL 18743 (A83543.8) or an A83543K-producing mutant thereof, in a suitable culture medium, under submerged aerobic fermentation conditions, until a recoverable amount of a compound of Formula 1 is produced. The Formula 1 compound can be isolated and purified as described herein.

Because strain NRRL 18743 is a newly discovered strain, this invention further provides a biologically purified culture of this microorganism.

The Formula 2 compounds are useful for the control of mites and insects, particularly Lepidoptera, Homoptera, and Diptera species. Therefore, insecticidal and miticidal compositions and methods for reducing the populations of insects and mites using these compounds are also a part of this invention.

DETAILED DESCRIPTION OF THE INVENTION

This invention is directed to compounds of the family of related components produced by *S. spinosa*. The general structure of the compounds of the present invention is shown in the following formula:

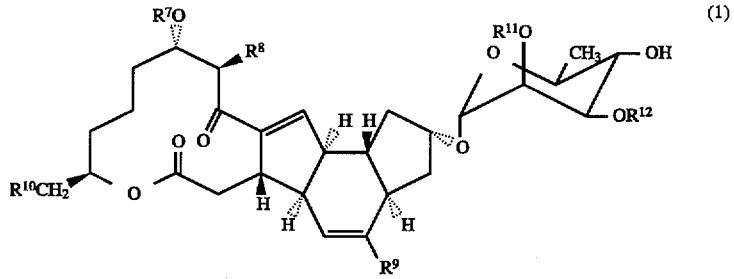

wherein $R^7$ is hydrogen or a group of formula

(a)

(b)

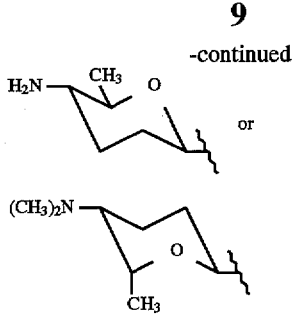

$R^8$, $R^9$, $R^{10}$, $R^{11}$, and $R^{12}$ are independently hydrogen or methyl, provided that $R^{11}$ and $R^{12}$ are not concurrently hydrogen; or an acid addition salt thereof when $R^7$ is other than hydrogen.

A preferred aspect of the invention is the Formula 1 compounds wherein $R^8$ and $R^{10}$ are methyl. A more preferred aspect of the invention is the Formula 1 compounds wherein $R^8$ and $R^{10}$ are methyl and $R^7$ is a group of formula

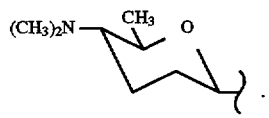

Another aspect of the present invention is new components of fermentation product A83543. These new A83543 components, termed Formula 2 compounds, have the following chemical structure:

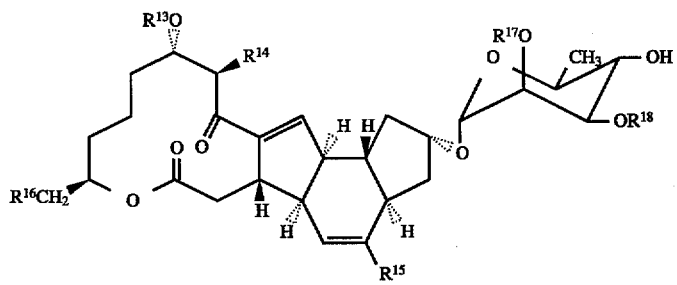

wherein $R^{13}$ is a group of formula

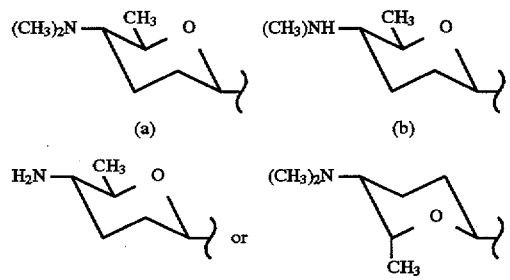

and $R^{14}$, $R^{15}$, $R^{16}$, $R^{17}$ and $R^{18}$ are independently hydrogen or methyl, provided that $R^{17}$ and $R^{18}$ are not concurrently hydrogen; or an acid addition salt thereof when $R^{13}$ is other than hydrogen.

A more preferred aspect of the present invention is the Formula 2 compounds wherein $R^{14}$ is $CH_3$ and $R^{13}$ is a group of formula

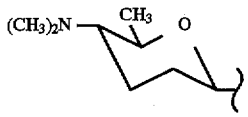

Preferably, this invention relates to new A83543 components, Formula 2 compounds, designated A83543K, A83543O, A83543P, A83543U, A83543V, A83543W, and A83543Y, wherein $R^{13}$, $R^{14}$, $R^{15}$, $R^{16}$, $R^{17}$ and $R^{18}$ are individually for each new component as follows:

| Component | $R^{13}$ | $R^{14}$ | $R^{15}$ | $R^{16}$ | $R^{17}$ | $R^{18}$ |
|---|---|---|---|---|---|---|
| K | (a) | $CH_3$ | H | $CH_3$ | $CH_3$ | $CH_3$ |
| O | (a) | $CH_3$ | $CH_3$ | $CH_3$ | $CH_3$ | $CH_3$ |
| P | (a) | $CH_3$ | H | $CH_3$ | $CH_3$ | H |
| U | (a) | $CH_3$ | H | $CH_3$ | H | $CH_3$ |
| V | (a) | $CH_3$ | $CH_3$ | $CH_3$ | H | $CH_3$ |
| W | (a) | $CH_3$ | $CH_3$ | $CH_3$ | $CH_3$ | H |
| Y | (a) | $CH_3$ | H | H | $CH_3$ | $CH_3$ |

The chemical structures of these new components were determined by spectrometric methods, including infrared spectroscopy (IR), nuclear magnetic resonance spectroscopy (NMR), and ultraviolet spectroscopy (UV), and by comparison to the A83543 components (see Kirst, et al. (1991), supra). The following paragraphs describe the physical and spectral properties of components A83543K, A83543O, A83543P, A83543U, A83543V, A83543W and A83543Y.

For the convenience of the reader, the following diagram of A83543K provides the position designations of all NMR spectral data for the A83543 natural factors presented below:

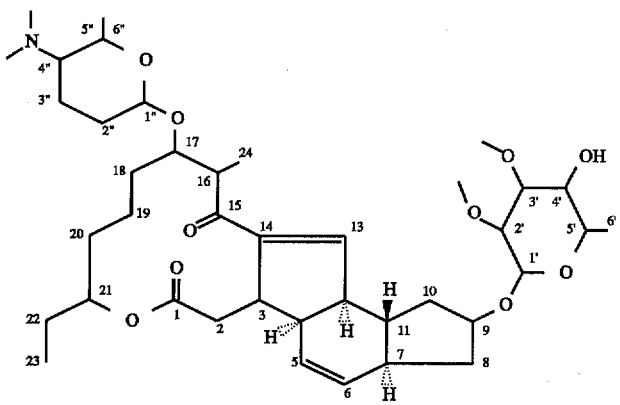

Figure 1:
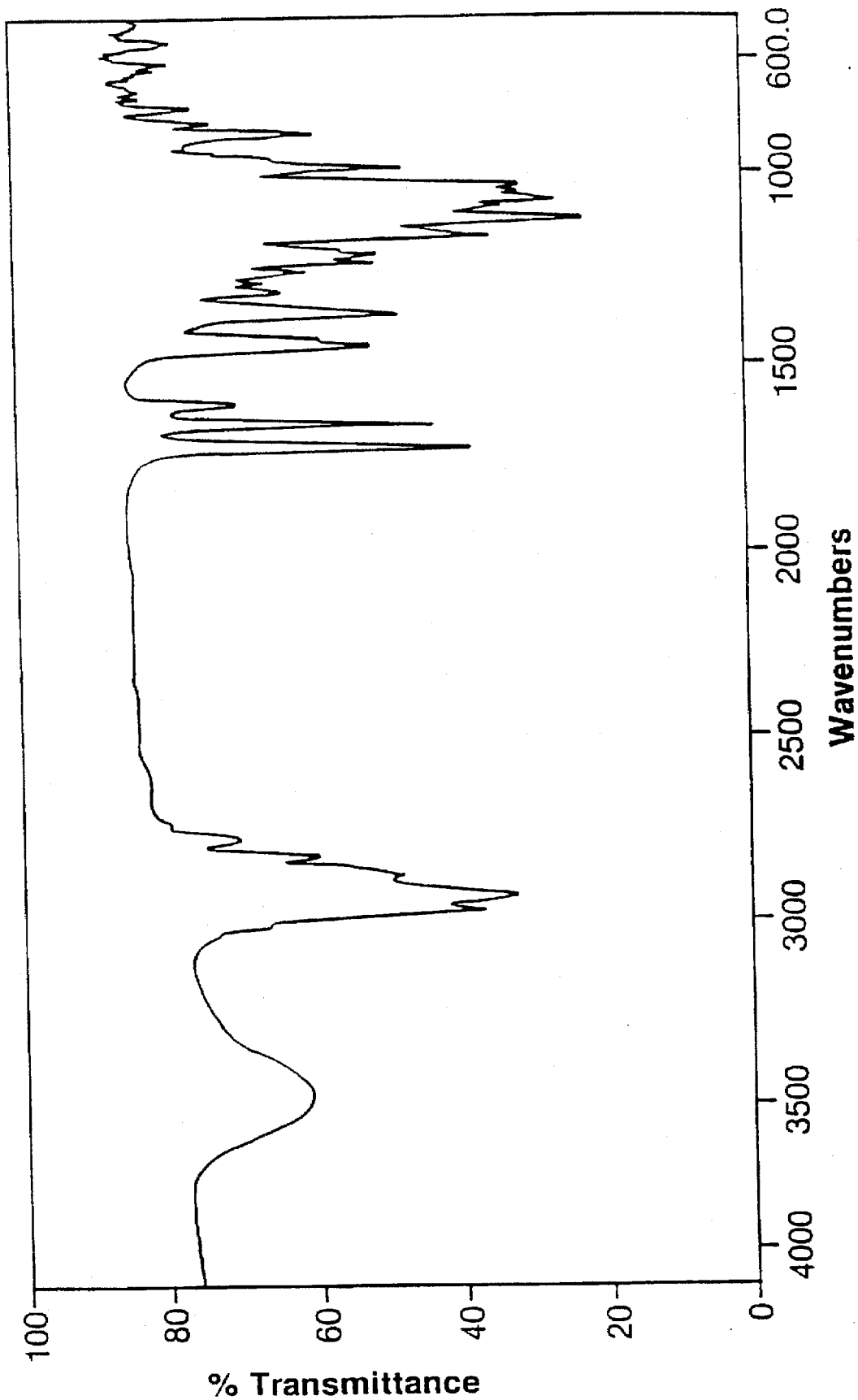
FIG. 1 shows the infrared absorption spectrum of A83543K in KBr.

A83543K:

A83543K has the following characteristics:
Molecular weight: 717
Empirical formula: $C_{40}H_{63}NO_{10}$
UV (EtOH): 243 nm ($\epsilon$=10,657)
MS (FAB): (M+H) m/z 718
IR (KBR): see FIG. 1.

Figure 2:
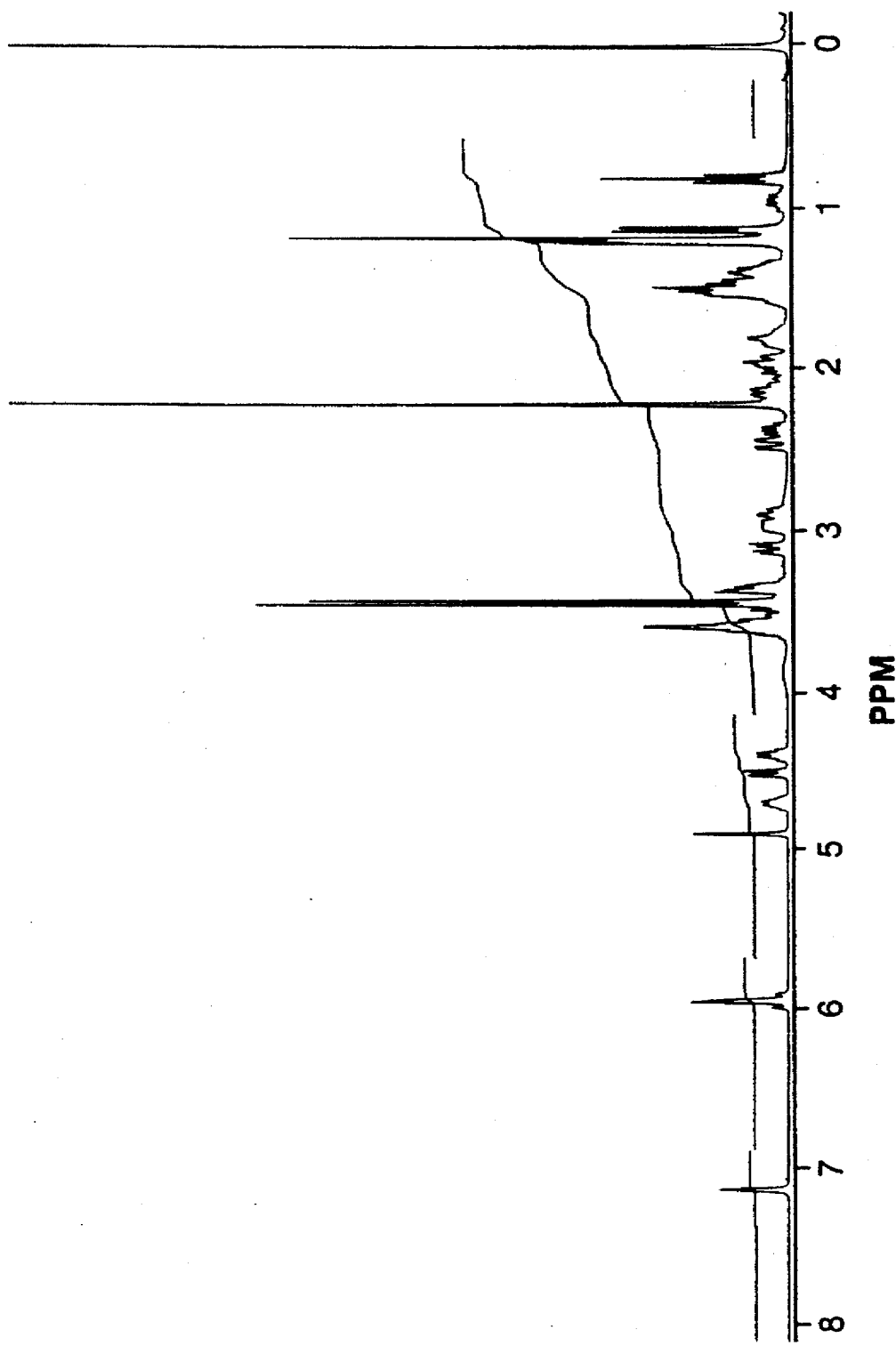
FIG. 2 shows the proton nuclear magnetic resonance spectrum of A83543K in acetone-$d_6$.

Table I summarizes the $^1H$ and $^{13}C$ NMR spectral data for A83453K (in acetone-$d_6$) as shown in FIG. 2.

TABLE I

| | $^1H$ and $^{13}C$ NMR data of A83543K in acetone-$d_6$ | |
|---|---|---|
| Position | $^{13}C$ | $^1H$* |
| 1 | 172.69 | — |
| 2 | 34.57 | 3.07/2.46 |
| 3 | 48.46 | 2.94 |
| 4 | 42.41 | 3.50 |
| 5 | 129.84 | 5.86 |
| 6 | 130.39 | 5.92 |
| 7 | 42.18 | 2.16 |
| 8 | 37.24 | 1.97/1.38 |
| 9 | 77.09 | 4.35 |
| 10 | 38.38 | 2.37/1.38 |
| 11 | 47.15 | 0.93 |
| 12 | 50.49 | 2.85 |
| 13 | 148.32 | 7.06 |
| 14 | 145.78 | — |
| 15 | 203.15 | — |
| 16 | 48.41 | 3.31 |
| 17 | 81.23 | 3.53 |
| 18 | 35.18 | 1.50 |
| 19 | 22.44 | 1.78/1.17 |
| 20 | 31.12 | 1.50 |
| 21 | 76.86 | 4.65 |
| 22 | 29.15 | 1.48 |
| 23 | 9.56 | 0.81 |
| 24 | 16.42 | 1.12 |
| 1' | 97.47 | 4.85 |
| 2' | 78.06 | 3.55 |
| 3' | 82.42 | 3.33 |
| 4' | 72.78 | 3.41 |
| 5' | 69.80 | 3.53 |
| 6' | 18.26 | 1.19 |
| 2'-OCH$_3$ | 59.02 | 3.42 |
| 3'-OCH$_3$ | 57.39 | 3.39 |
| 1" | 104.20 | 4.46 |
| 2" | 32.02 | 1.94/1.38 |
| 3" | 18.93 | 1.81/1.48 |
| 4" | 66.10 | 2.11 |
| 5" | 74.17 | 2.56 |

TABLE I-continued

| | $^1H$ and $^{13}C$ NMR data of A83543K in acetone-$d_6$ | |
|---|---|---|
| Position | $^{13}C$ | $^1H$* |
| 6" | 19.44 | 1.20 |
| N(CH$_3$)$_2$ | 41.02 | 2.21 |

*Some assignments are from $^1H/^{13}C$ correlations.

Figure 3:
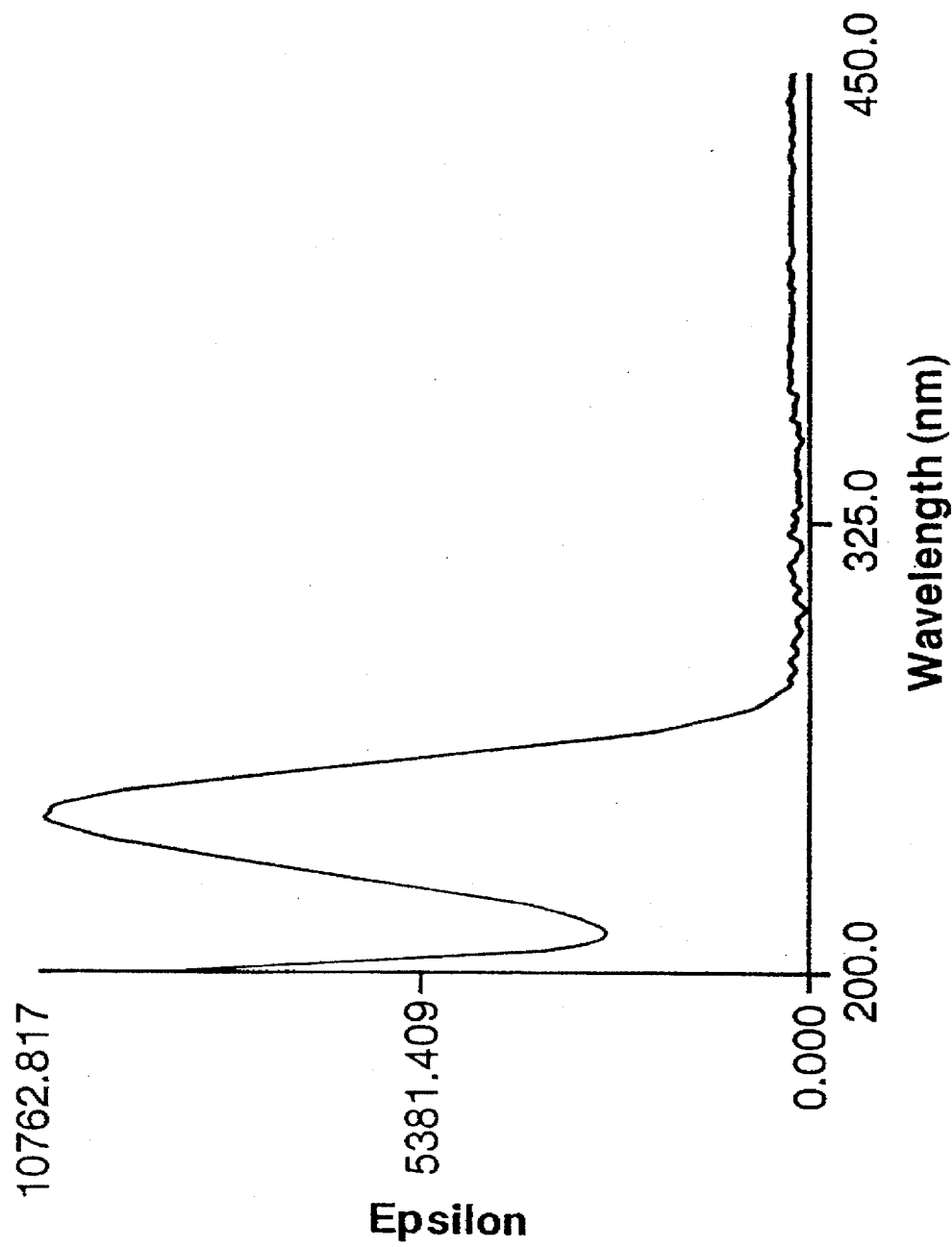
FIG. 3 shows the UV spectrum spectrum of A83543K in EtOH.

A83543K has the following characteristics:
Molecular weight: 731
Empirical formula: $C_{41}H_{65}NO_{10}$
UV (EtOH): 243 nm ($\epsilon$=9,267)
FD (M+) m/z 731
IR (KBr): see FIG. 3.

Figure 4:
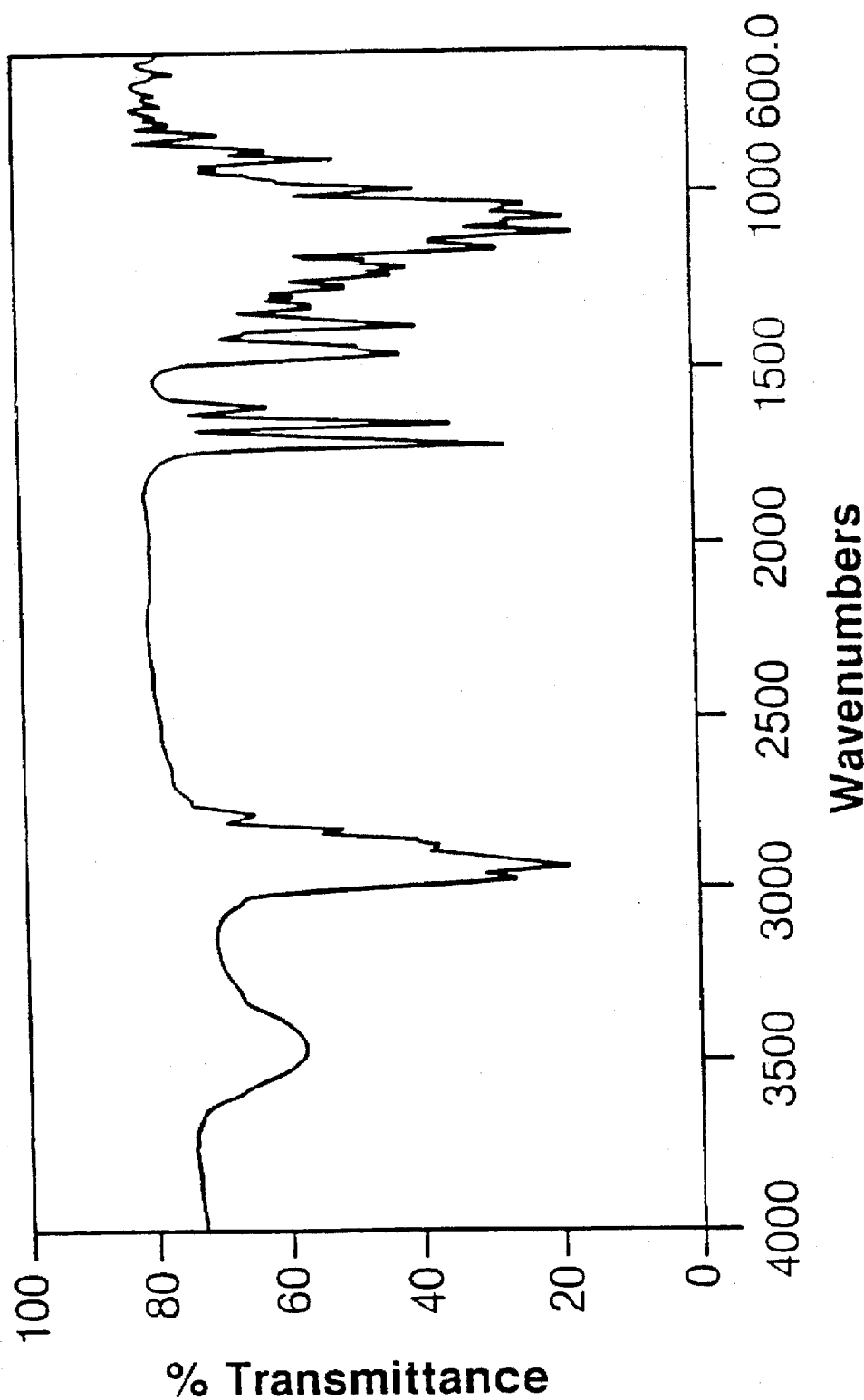
FIG. 4 shows the infrared absorption spectrum of A83543O in KBr.

Table II summarizes the $^1H$ and $^{13}C$ nuclear magnetic resonance (NMR) spectral data for A83454O (in acetone-$d_6$) as shown in FIG. 4.

TABLE II

| | $^1H$ and $^{13}C$ NMR data of A83543O in acetone-$d_6$ | |
|---|---|---|
| Position | $^{13}C$ | $^1H$* |
| 1 | 172.60 | — |
| 2 | 34.29 | 3.08/2.42 |
| 3 | 48.88 | 2.91 |
| 4 | 42.71 | 3.45 |
| 5 | 123.26 | 5.55 |
| 6 | 137.16 | — |
| 7 | 45.32 | 2.19 |
| 8 | 35.52 | 2.02/1.45 |
| 9 | 76.80 | 4.64 |
| 10 | 38.59 | 2.37/1.41 |
| 11 | 46.92 | 1.03 |
| 12 | 49.94 | 2.78 |
| 13 | 148.46 | 7.03 |
| 14 | 145.07 | — |
| 15 | 203.09 | — |
| 16 | 48.39 | 3.30 |
| 17 | 80.88 | 3.55 |
| 18 | 35.00 | 1.50 |
| 19 | 22.49 | 1.80/1.17 |
| 20 | 30.84 | 1.50 |
| 21 | 76.50 | 4.34 |
| 22 | 29.08 | 1.48 |
| 23 | 9.54 | 0.80 |
| 24 | 16.26 | 1.13 |
| 6-CH$_3$ | 20.85 | 1.73 |
| 1' | 97.21 | 4.87 |

TABLE II-continued

¹H and ¹³C NMR data of A83543O in acetone-$d_6$

| Position | ¹³C | ¹H* |
|---|---|---|
| 2' | 77.80 | 3.56 |
| 3' | 82.23 | 3.33 |
| 4' | 72.54 | 3.41 |
| 5' | 69.61 | 3.55 |
| 6' | 18.21 | 1.19 |
| 2'-OCH₃ | 58.96 | 3.41 |
| 3'-OCH₃ | 57.31 | 3.39 |
| 1" | 104.02 | 4.46 |
| 2" | 31.85 | 1.94/1.39 |
| 3" | 18.74 | 1.82/1.52 |
| 4" | 65.90 | 2.12 |
| 5" | 73.90 | 3.57 |
| 6" | 19.39 | 1.20 |
| N(CH₃)₂ | 40.92 | 2.20 |

*Values were taken from a heteronuclear one bond 2D correlation spectrum.

Figure 5:
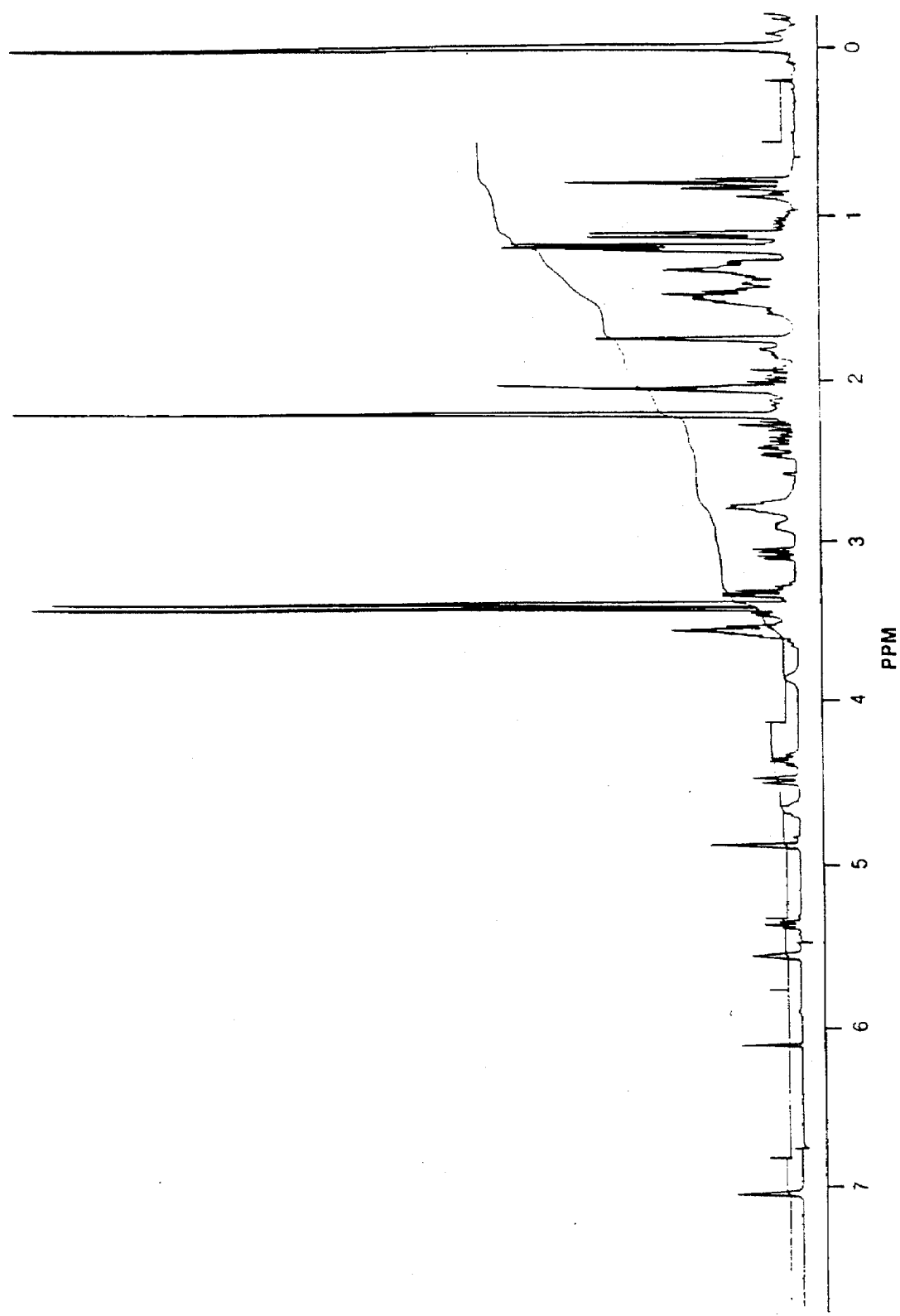
FIG. 5 shows the proton nuclear magnetic resonance spectrum of A83543O in acetone-$d_6$.

A83543P has the following characteristics:
Molecular weight: 703
Empirical formula: $C_{39}H_{61}NO_{10}$
UV (EtOH): 243 nm ($\epsilon$=13,760)
MS (FAB): (M+H) m/z 704
IR (KBr): see FIG. 5.

Figure 6:
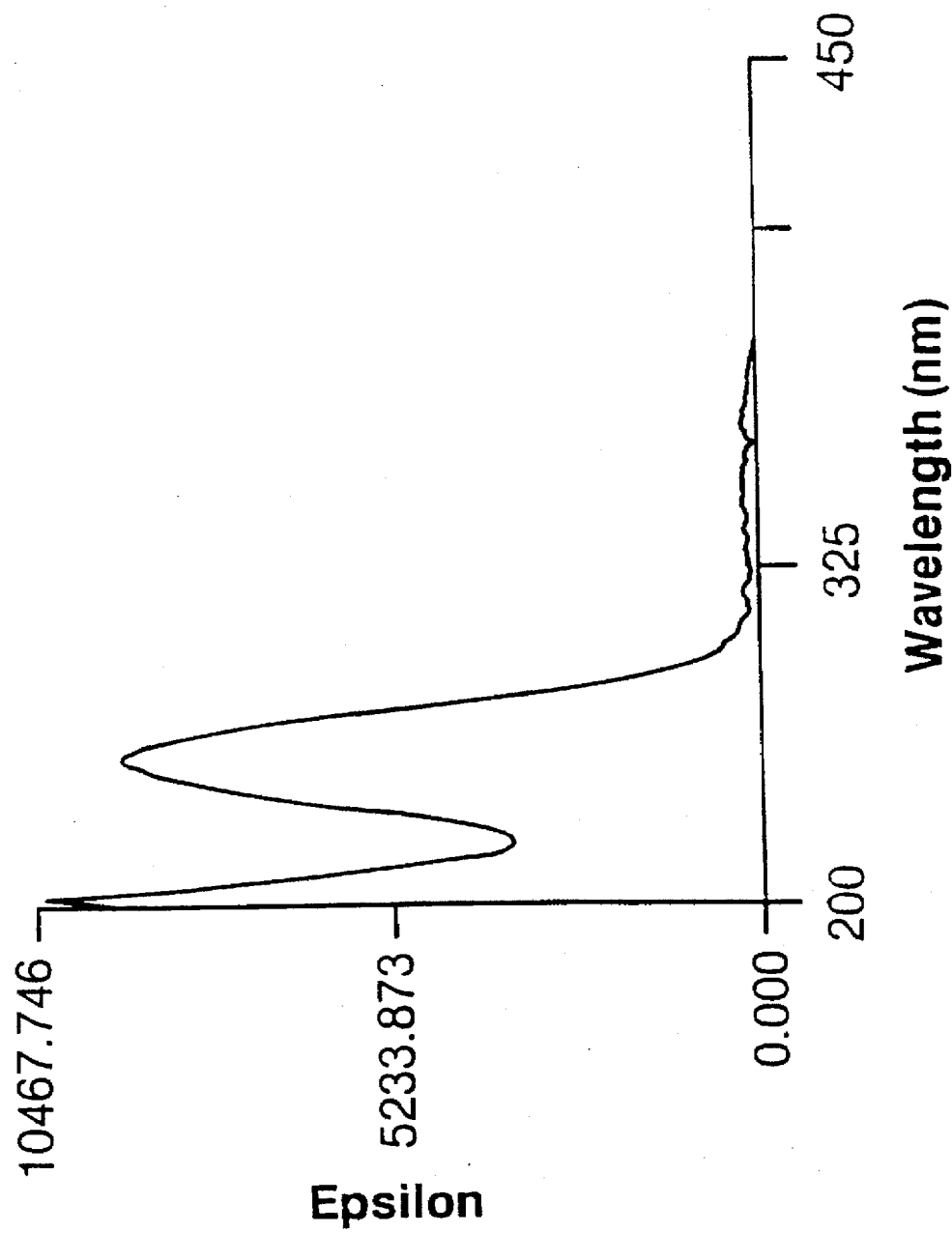
FIG. 6 shows the UV spectrum spectrum of A83543O in EtOH.

Table III summarizes the ¹H and ¹³C nuclear magnetic resonance (NMR) spectral data for A83454P (in acetone-$d_6$) as shown in FIG. 6.

TABLE III

¹H and ¹³C NMR data of A83543P in acetone-$d_6$

| Position | ¹³C | ¹H* |
|---|---|---|
| 1 | 172.62 | — |
| 2 | 34.43 | 3.06/2.44 |
| 3 | 48.74 | 2.94 |
| 4 | 42.26 | 3.50 |
| 5 | 129.70 | 5.86 |
| 6 | 130.30 | 5.89 |
| 7 | 42.06 | 2.14 |
| 8 | 37.15 | 1.97/1.34 |
| 9 | 76.84 | 4.34 |
| 10 | 38.28 | 2.36/1.36 |
| 11 | 47.05 | 0.92 |
| 12 | 50.37 | 2.86 |
| 13 | 148.43 | 7.03 |
| 14 | 144.85 | — |
| 15 | 203.09 | — |
| 16 | 48.35 | 3.31 |
| 17 | 80.96 | 3.55 |
| 18 | 35.06 | 1.50 |
| 19 | 22.44 | 1.78/1.16 |
| 20 | 30.91 | 1.55 |
| 21 | 76.84 | 4.64 |
| 22 | 29.11 | 1.47 |
| 23 | 9.55 | 0.80 |
| 24 | 16.29 | 1.11 |
| 1' | 96.68 | 4.86 |
| 2' | 82.07 | 3.33 |
| 3' | 72.41 | 3.63 |
| 4' | 74.27 | 3.30 |
| 5' | 69.45 | 3.53 |
| 6' | 18.17 | 1.19 |
| 2'-OCH₃ | 59.12 | 3.41 |
| 1" | 104.08 | 4.45 |
| 2" | 31.89 | 1.92/1.37 |
| 3" | 18.72 | 1.81/1.52 |
| 4" | 65.97 | 2.11 |
| 5" | 74.03 | 3.56 |

TABLE III-continued

¹H and ¹³C NMR data of A83543P in acetone-$d_6$

| Position | ¹³C | ¹H* |
|---|---|---|
| 6" | 19.39 | 1.19 |
| N(CH₃)₂ | 40.95 | 2.20 |

*Values were taken from a heteronuclear one bond 2D correlation spectrum.

Figure 7:
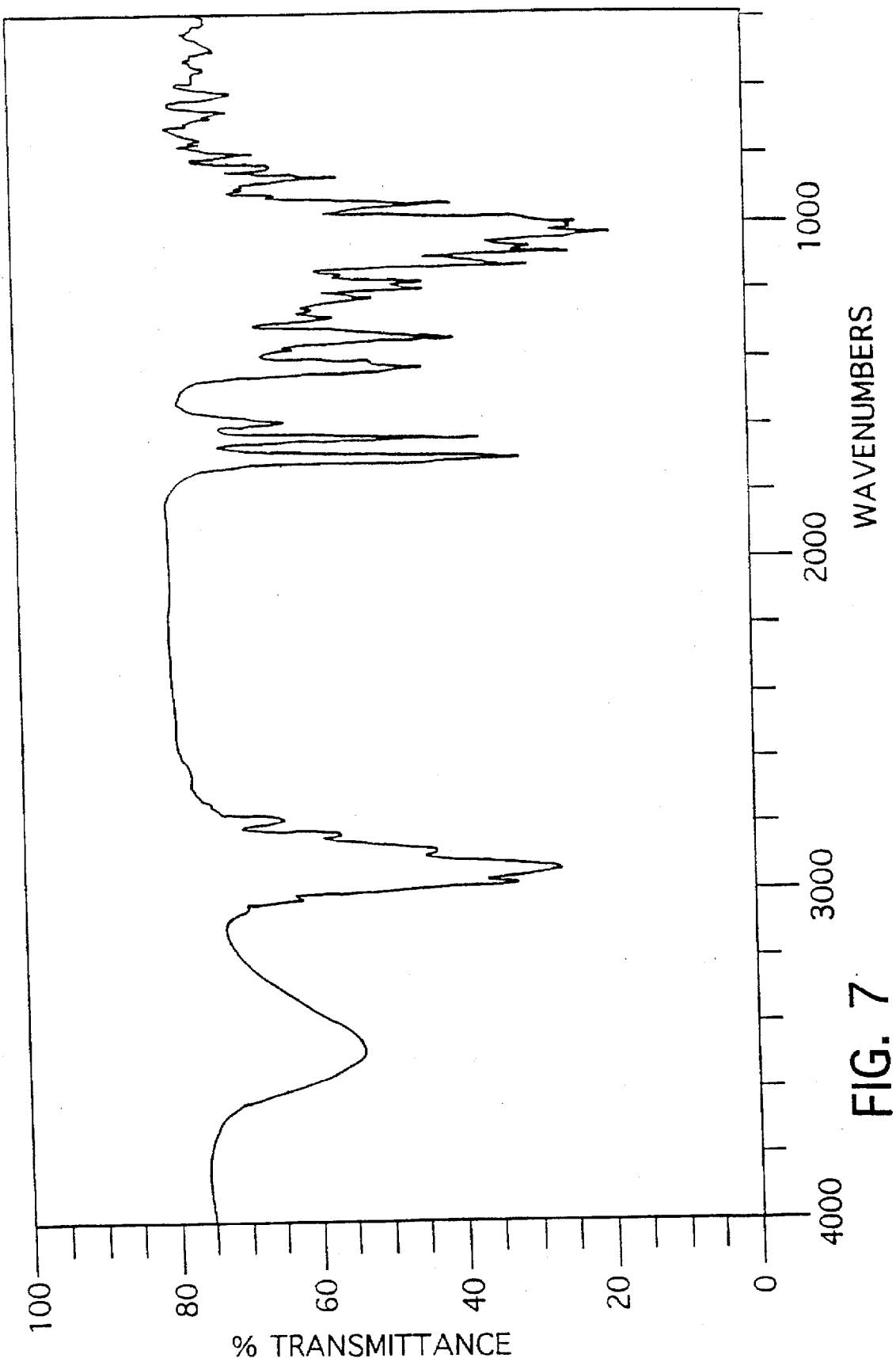
FIG. 7 shows the infrared absorption spectrum of A83543P in KBr.

A83543U:
A83543U has the following characteristics:
Molecular weight: 703
Empirical formula: $C_{39}H_{61}NO_{10}$
UV (EtOH): 242 nm ($\epsilon$=17,095)
MS (FAB): (M+H) m/z 704
IR (KBr): see FIG. 7.

Figure 8:
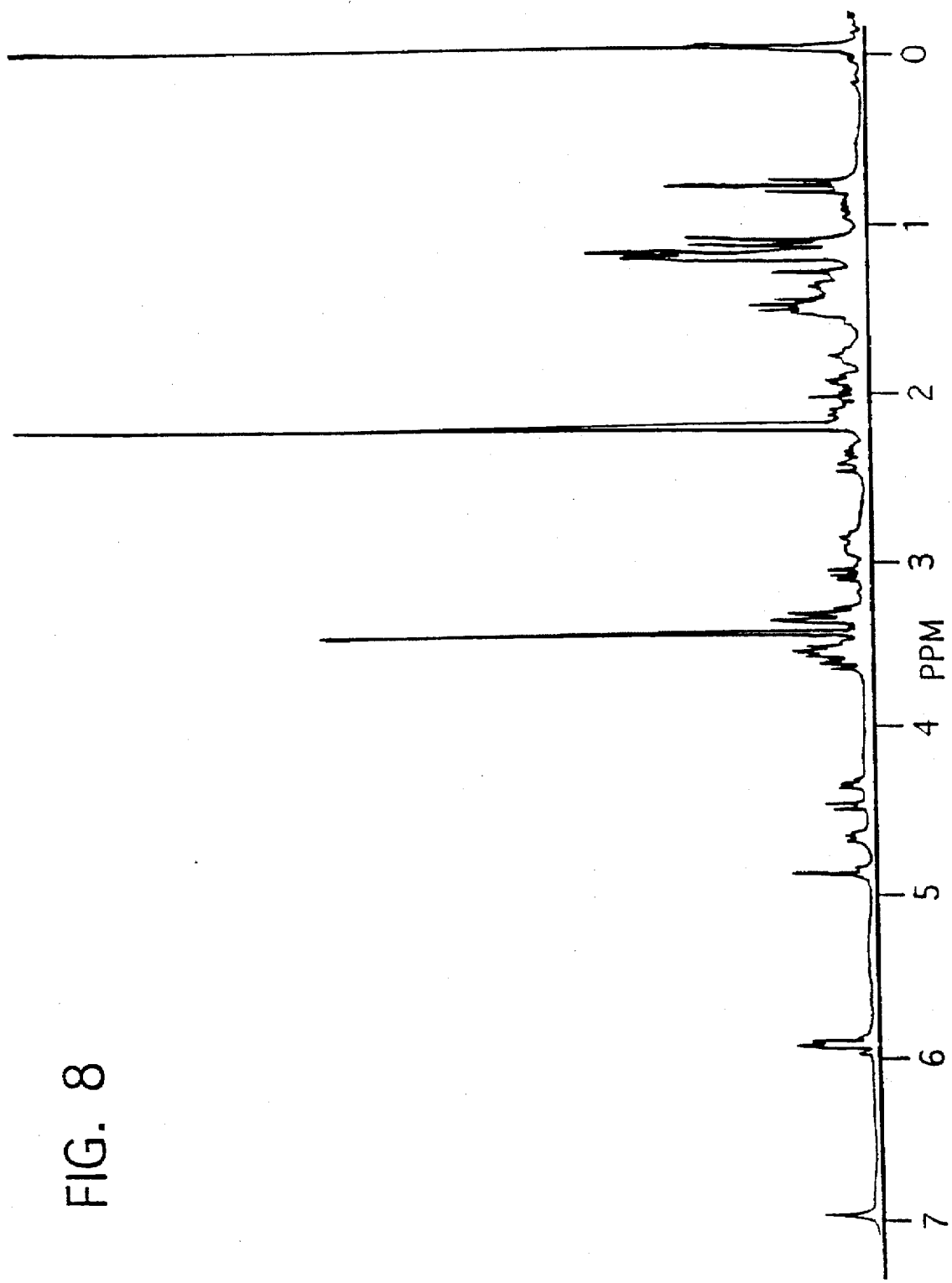
FIG. 8 shows the proton nuclear magnetic resonance spectrum of A83543P in acetone-$d_6$.

Table IV summarizes the ¹H and ¹³C nuclear magnetic resonance (NMR) spectral data for A83454U (in acetone-$d_6$) as shown in FIG. 8.

TABLE IV

¹H and ¹³C NMR data of A83543U in acetone-$d_6$

| Position | ¹³C | ¹H* |
|---|---|---|
| 1 | 172.68 | — |
| 2 | 34.53 | 3.10/2.49 |
| 3 | 48.41 | 2.97 |
| 4 | 42.15 | 3.54 |
| 5 | 129.77 | 5.91 |
| 6 | 130.39 | 5.93 |
| 7 | 42.37 | 2.19 |
| 8 | 37.16 | 2.00/1.41 |
| 9 | 76.81** | 4.38 |
| 10 | 38.82 | 2.41/1.42 |
| 11 | 47.13 | 0.97 |
| 12 | 50.46 | 2.91 |
| 13 | 148.37 | 7.09 |
| 14 | 144.96 | — |
| 15 | 203.10 | — |
| 16 | 48.63 | 3.35 |
| 17 | 81.15 | 3.57 |
| 18 | 35.15 | 1.57/1.51 |
| 19 | 22.45 | 1.82/1.21 |
| 20 | 31.06 | 1.58/1.49 |
| 21 | 76.85** | 4.69 |
| 22 | 29.04 | 1.54/1.50 |
| 23 | 9.57 | 0.83 |
| 24 | 16.39 | 1.16 |
| 1' | 99.92 | 4.80 |
| 2' | 68.34 | 3.97 |
| 3' | 82.36 | 3.2 |
| 4' | 72.45 | 3.48 |
| 5' | 69.42 | 3.62 |
| 6' | 18.21 | 1.24 |
| 3'-OCH₃ | 57.06 | 3.42 |
| 1" | 104.16 | 4.49 |
| 2" | 31.98 | 1.97/1.42 |
| 3" | 18.67 | 1.86/1.55 |
| 4" | 66.06 | 2.14 |
| 5" | 73.14 | 3.60 |
| 6" | 19.43 | 1.24 |
| N(CH₃)₂ | 41.01 | 2.24 |

*Values were taken from 1D or inverse 2D one bond correlation spectrum.
**Assignments may be reversed.

A83543V:
A83543V has the following characteristics:
Molecular weight: 717
Empirical formula: $C_{40}H_{63}NO_{10}$
UV (EtOH): 242 nm ($\epsilon$=10,140)
MS (FAB): (M+H) m/z 718

Figure 9:
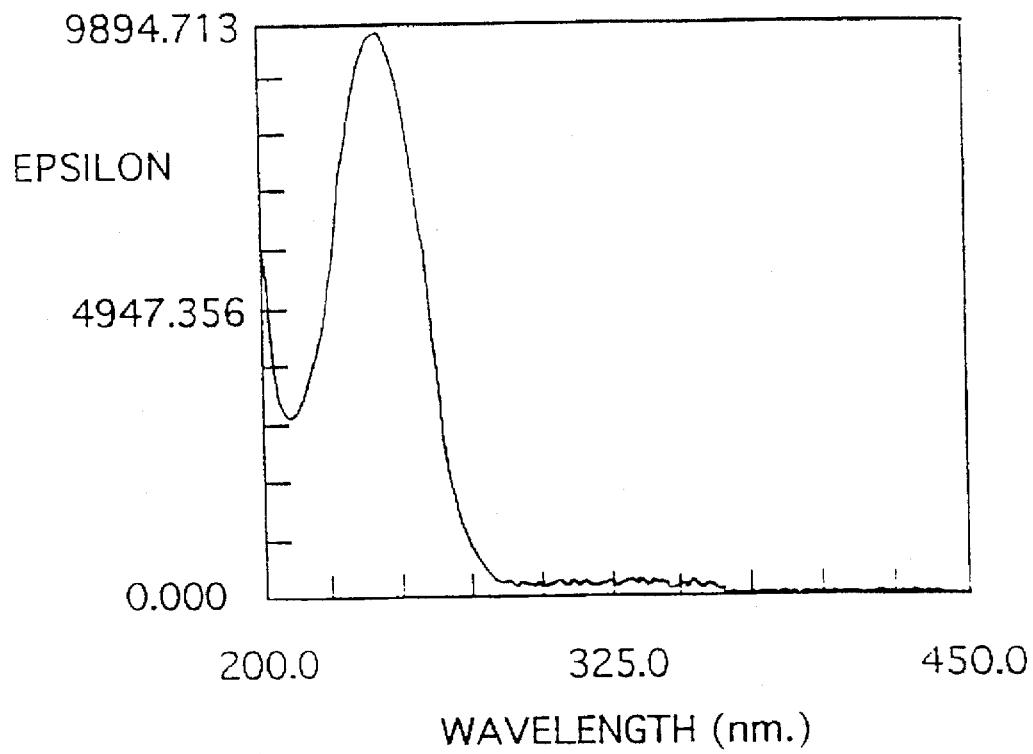
FIG. 9 shows the UV spectrum spectrum of A83543P in EtOH.

IR (KBr): see FIG. 9.

Figure 10:
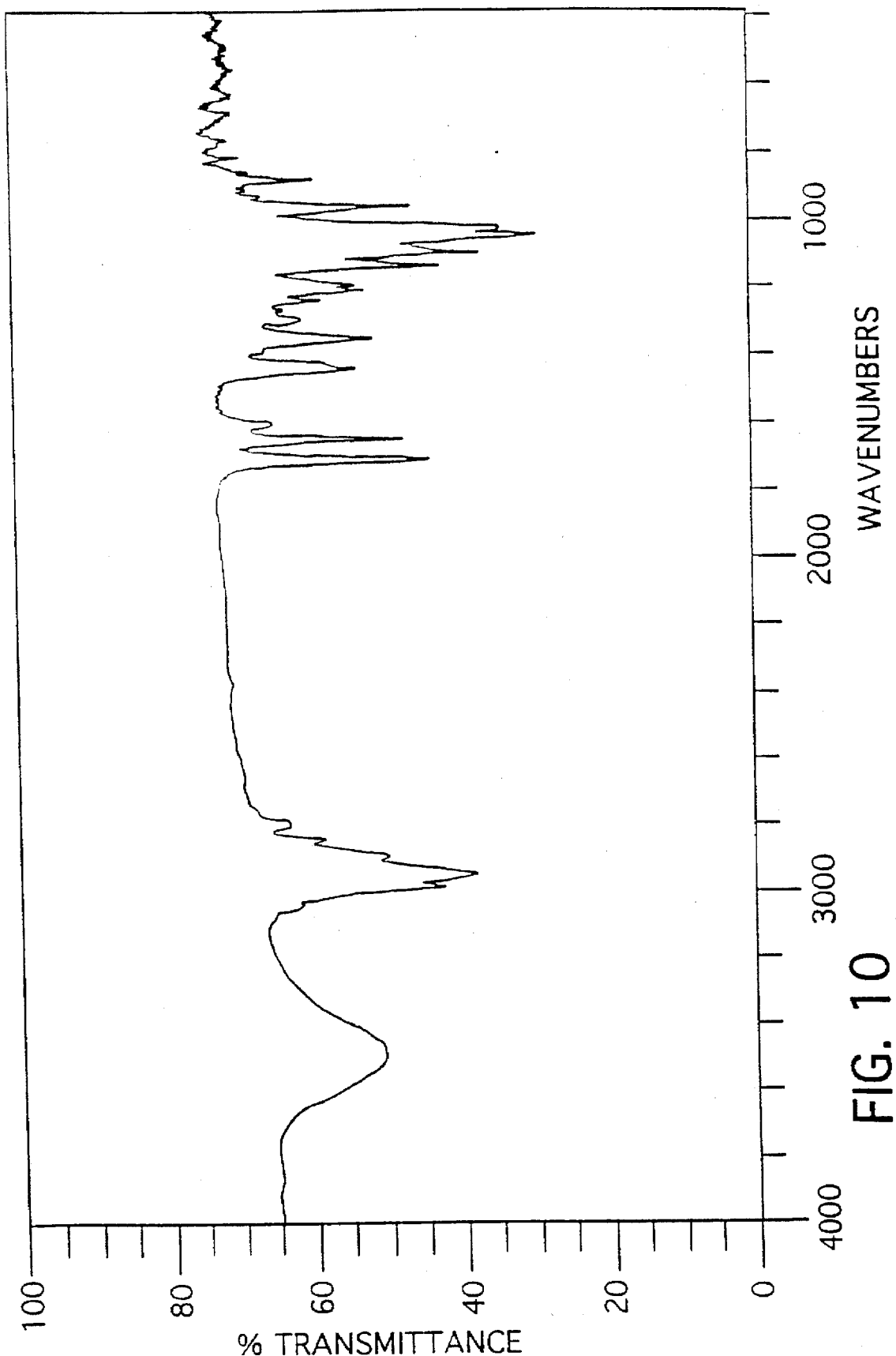
FIG. 10 shows the infrared absorption spectrum of A83543U in KBr.

Table V summarizes the $^1$H and $^{13}$C nuclear magnetic resonance (NMR) spectral data for A83454V (in acetone-$d_6$) as shown in FIG. 10.

TABLE V $^1$H and $^{13}$C NMR data of A83543V in acetone-$d_6$

| Position | $^{13}$C | $^1$H* |
|---|---|---|
| 1 | 172.63 | — |
| 2 | 34.34 | 3.10/2.45 |
| 3 | 48.88 | 2.88 |
| 4 | 42.63 | 3.49 |
| 5 | 123.20 | 5.57 |
| 6 | 137.25 | — |
| 6-CH$_3$ | 20.77 | 1.76 |
| 7 | 45.23 | 2.21 |
| 8 | 35.44 | 2.02/1.45 |
| 9 | 76.22 | 4.36 |
| 10 | 38.63 | 2.40/1.41 |
| 11 | 46.89 | 1.07 |
| 12 | 49.92 | 2.80 |
| 13 | 148.54 | 7.08 |
| 14 | 145.10 | — |
| 15 | 203.11 | — |
| 16 | 48.46 | 3.34 |
| 17 | 80.80 | 3.56 |
| 18 | 35.12 | 1.54/1.50 |
| 19 | 22.50 | 1.82/1.21 |
| 20 | 30.81 | 1.56/1.51 |
| 21 | 76.71 | 4.67 |
| 22 | 29.01 | 1.51 |
| 23 | 9.38 | 0.82 |
| 24 | 16.17 | 1.14 |
| 1' | 99.88 | 4.67 |
| 2' | 69.03 | 3.69 |
| 3' | 82.19 | 3.29 |
| 4' | 72.21 | 3.46 |
| 5' | 68.18 | 3.61 |
| 6' | 18.04 | 1.22 |
| 3'-OCH$_3$ | 56.98 | 3.41 |
| 1" | 104.14 | 4.49 |
| 2" | 31.91 | 1.95/1.41 |
| 3" | 18.62 | 1.84/1.54 |
| 4" | 65.92 | 2.14 |
| 5" | 73.92 | 3.59 |
| 6" | 19.31 | 1.22 |
| N(CH$_3$)$_2$ | 40.78 | 2.23 |

*Values were taken from 1D and 2D inverse experiments

Figure 11:
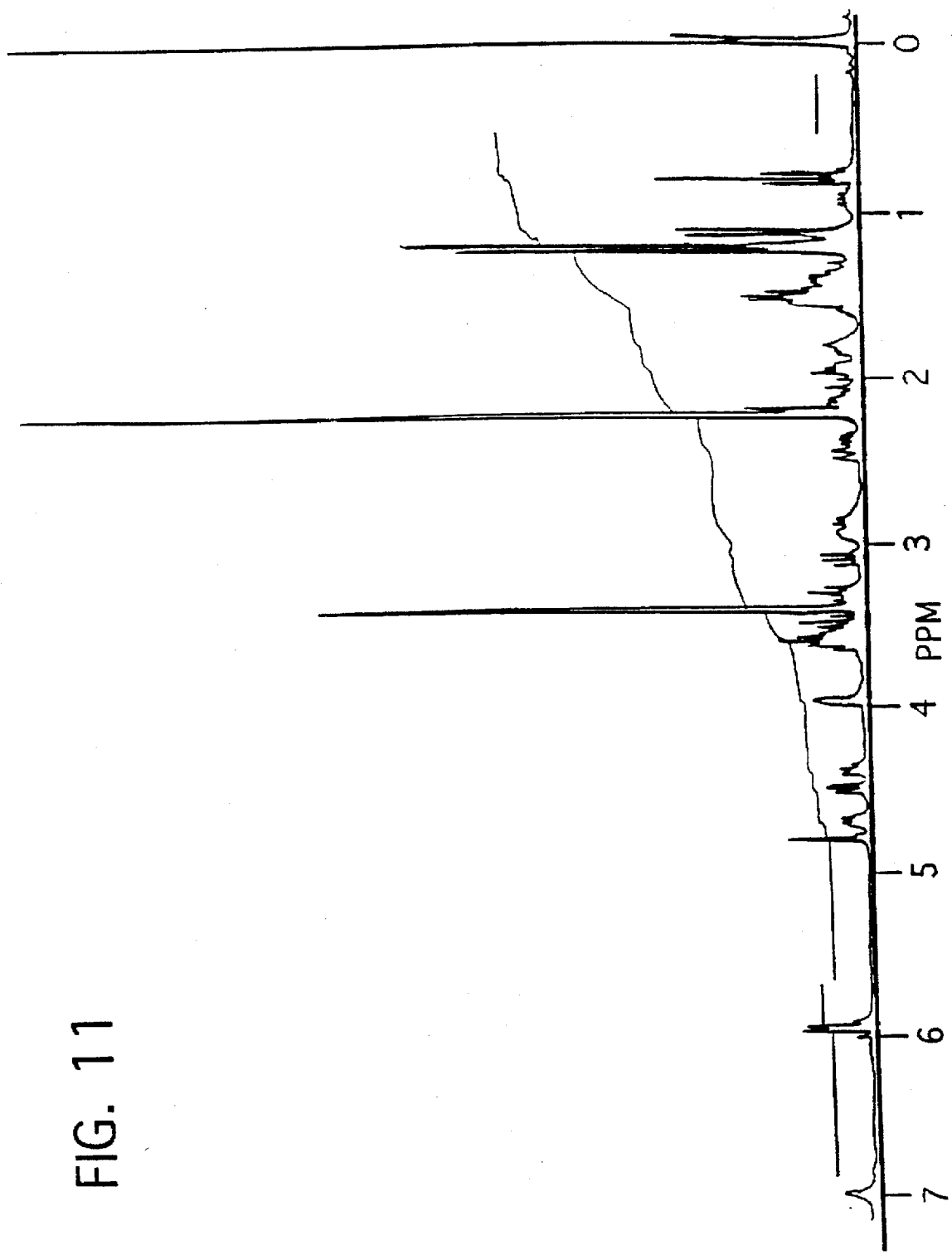
FIG. 11 shows the proton nuclear magnetic resonance spectrum of A83543U in acetone-$d_6$.

A83543W:

A83543W has the following characteristics:
Molecular weight: 717
Empirical formula: $C_{40}H_{63}NO_{10}$
UV (EtOH): 244 nm ($\epsilon$=10,254)
MS (FAB): (M+H) m/z 718
IR (KBr): see FIG. 11

Figure 12:
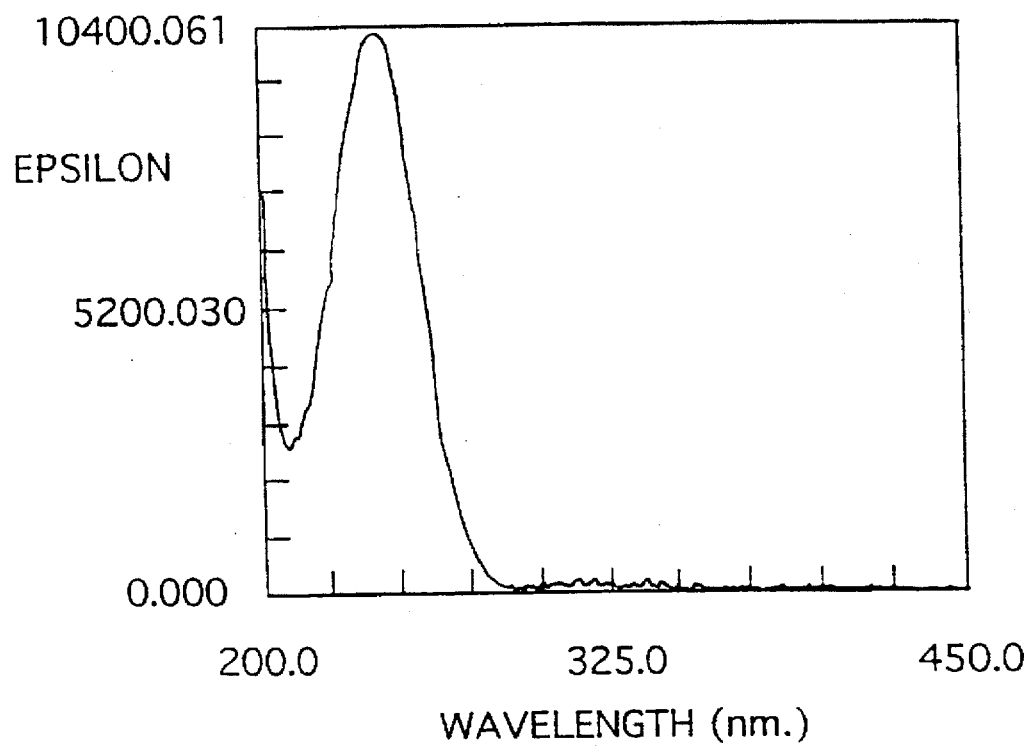
FIG. 12 shows the UV spectrum spectrum of A83543U in EtOH.

Table VI summarizes the $^1$H and $^{13}$C nuclear magnetic resonance (NMR) spectral data for A83543W (in acetone-$d_6$) as shown in FIG. 12.

TABLE VI $^1$H and $^{13}$C NMR data of A83543W in acetone-$d_6$

| Position | $^{13}$C | $^1$H* |
|---|---|---|
| 1 | 172.62 | — |
| 2 | 34.46 | 3.08/2.44 |
| 3 | 49.00 | 2.90 |
| 4 | 42.69 | 3.46 |
| 5 | 123.52 | 5.55 |
| 6 | 137.25 | — |

TABLE VI-continued $^1$H and $^{13}$C NMR data of A83543W in acetone-$d_6$

| Position | $^{13}$C | $^1$H* |
|---|---|---|
| 6-CH$_3$ | 20.93 | 1.76 |
| 7 | 45.58 | 2.21 |
| 8 | 35.83 | 2.04/1.46 |
| 9 | 76.67 | 4.35 |
| 10 | 38.81 | 2.39/1.41 |
| 11 | 47.27 | 1.04 |
| 12 | 50.09 | 2.80 |
| 13 | 146.41 | 7.04 |
| 14 | 145.15 | — |
| 15 | 203.11 | — |
| 16 | 48.45 | 3.32 |
| 17 | 81.05 | 3.56 |
| 18 | 35.19 | 1.51 |
| 19 | 22.62 | 1.81/1.19 |
| 20 | 31.08 | 1.51 |
| 21 | 76.94 | 4.66 |
| 22 | 29.31 | 1.49 |
| 23 | 9.58 | 0.80 |
| 24 | 16.26 | 1.11 |
| 1' | 96.94 | 4.88 |
| 2' | 82.42 | 3.34 |
| 3' | 72.56 | 3.64 |
| 4' | 74.48 | 3.32 |
| 5' | 69.54 | 3.56 |
| 6' | 18.27 | 1.20 |
| 2'-OCH$_3$ | 59.13 | 3.43 |
| 1" | 104.34 | 4.47 |
| 2" | 32.13 | 1.95/1.40 |
| 3" | 18.84 | 1.83/1.54 |
| 4" | 66.26 | 2.12 |
| 5" | 74.20 | 3.59 |
| 6" | 19.56 | 1.21 |
| N(CH$_3$)$_2$ | 41.15 | 2.22 |

*Values taken from $^1$H/$^{13}$C inverse one bond correlation spectra.

A83543Y has the following characteristics:
Molecular weight: 703
Empirical formula: $C_{39}H_6NO_{10}$
UV (EtOH): 243 nm ($\epsilon$=14,042)
MS (FAB): (M+H) m/z 704
IR (KBr): see FIG. 11

Table VII summarizes the $^1$H and $^{13}$C nuclear magnetic resonance (NMR) spectral data for A83543Y (in acetone-$d_6$) as shown in FIG. 12.

TABLE VII $^1$H and $^{13}$C NMR data of A83543Y in acetone-$d_6$

| Position | $^{13}$C | $^1$H* |
|---|---|---|
| 1 | 172.42 | — |
| 2 | 34.86 | 3.07/2.42 |
| 3 | 48.80 | 2.96 |
| 4 | 42.04** | 3.44 |
| 5 | 129.68 | 5.87 |
| 6 | 130.32 | 5.91 |
| 7 | 42.00** | 2.16 |
| 8 | 37.08 | 1.98/1.38 |
| 9 | 76.86 | 4.35 |
| 10 | 38.26 | 2.38/1/39 |
| 11 | 47.07 | 0.94 |
| 12 | 50.30 | 2.87 |
| 13 | 148.45 | 7.06 |
| 14 | 144.72 | — |
| 15 | 203.06 | — |
| 16 | 47.97 | 3.35 |
| 17 | 81.23 | 3.56 |
| 18 | 34.86 | 1.61/1.52 |

TABLE VII-continued

¹H and ¹³C NMR data of
A83543Y in acetone-$d_6$

| Position | ¹³C | ¹H* |
|---|---|---|
| 19 | 22.22 | 1.78/1.19 |
| 20 | 33.56 | 1.54/1.47 |
| 21 | 72.97 | 4.69 |
| 22 | 21.58 | 1.12 |
| 23 | — | — |
| 24 | 16.42 | 1.13 |
| 1' | 97.24 | 4.85 |
| 2' | 77.81 | 3.55 |
| 3' | 82.25 | 3.31 |
| 4' | 72.61 | 3.41 |
| 5' | 69.64 | 3.55 |
| 6' | 18.21 | 1.19 |
| 2'-OCH₃ | 58.94 | 3.41 |
| 3'-OCH₃ | 57.28 | 3.40 |
| 1" | 104.16 | 4.47 |
| 2" | 31.90 | 1.94/1.41 |
| 3" | 18.71 | 1.82/1.53 |
| 4" | 65.94 | 2.12 |
| 5" | 74.02 | 3.57 |
| 6" | 19.37 | 1.21 |
| N(CH₃)₂ | 40.93 | 2.22 |

*Data obtained from 1D, inverse heteronuclear correlation, homonuclear decoupling and COSY experiments.
**Assignments may be reversed Components A83543K, A83543O, A83543P, A83543U, A83543V, A83543W and A83543Y are structurally distinct from previously described compounds. The present compounds possess neutral sugars which have not been previously described: components A83543K, A83543O and A83543Y have a neutral sugar identified as α-2,3-di-O-methylrhamnose; components A83543P and A83543W have a neutral sugar identified as 2-O-methylrhamnose; components A83543U and A83543V have a neutral sugar identified as 3-O-methylrhamnose.

The amino sugar can be selectively removed from the new A83543 components to give new A83543 pseudoaglycones, termed Formula 3 compounds. These compounds are a further aspect of the present invention and are the compounds of Formula 1 wherein $R^1$ is hydrogen.

The selective removal of the amino sugar from A83543K, A83543O, A83543P, A83543U, A83543V, A83543W and A83543Y produces A83543K pseudoaglycone, A83543O pseudoaglycone, A83543P pseudoaglycone, A83543U pseudoaglycone, A83543V pseudoaglycone, A83543W pseudoaglycone, and A83543Y pseudoaglycone respectively. These compounds are shown in the following formula:

| Compound | $R^{19}$ | $R^{20}$ | $R^{21}$ | $R^{22}$ |
|---|---|---|---|---|
| A83543K pseudoaglycone | H | CH₃ | CH₃ | CH₃ |
| A83543O pseudoaglycone | CH₃ | CH₃ | CH₃ | CH₃ |
| A83543P pseudoaglycone | H | CH₃ | CH₃ | H |
| A83543U pseudoaglycone | H | CH₃ | H | CH₃ |
| A83543V pseudoaglycone | CH₃ | CH₃ | H | CH₃ |
| A83543W pseudoaglycone | CH₃ | CH₃ | CH₃ | H |
| A83543Y pseudoaglycone | H | H | CH₃ | CH₃ |

The Formula 2 compounds are used to prepare the Formula 3 compounds by the reaction of a Formula 2 compound with acid to remove the amino sugar. Suitable acids include hydrochloric and sulfuric, the preferred acid for the transformation is sulfuric. The reaction is preferably carried out in a polar organic solvent, a mixture of a polar organic solvent and water, or water. Suitable organic solvents include methanol, THF, acetonitrile and dioxane. The preferred solvents for the transformation are a mixture of methanol and water or water. The reaction may be carried out at a temperature from about 25° C. to about 95° C., preferably at 80° C.

The pseudoaglycones are useful as starting materials for the preparation of new A83543 compounds, for example, the pseudoaglycone may be glycosylated at the hydroxyl group where the amino sugar was present. This glycosylation may be carried out by chemical synthesis or by microbial bioconversion.

Another aspect of the present invention is the chemical demethylation of certain Formula 1 compounds. The Formula 1 compounds may be grouped into 3 subgroups: 1A, 1B and 1C. The Formula 1A compounds are the Formula 1 compounds wherein $R^7$ is a group of formula:

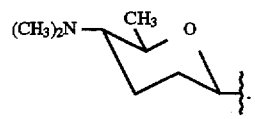

The Formula 1B compounds are the Formula 1 compounds wherein $R^7$ is a group of formula:

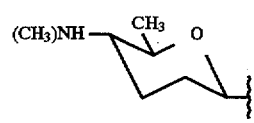

The Formula 1C compounds are the Formula 1 compounds wherein $R^7$ is a group of formula:

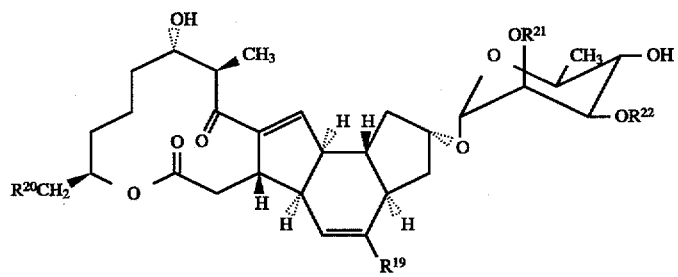

(3)

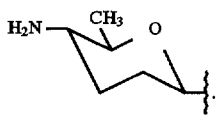

As described herein, the Formula 1B compounds may be prepared from the Formula 1A compounds. Similarly, the Formula 1C compounds may be prepared from the Formula 1B compounds. These compounds may be prepared by chemical demethylation of a corresponding new A83543 component. Each of these sub-groups is also a subset of the Formula 2 compounds.

The N-demethyl derivatives, the Formula 1B compounds, are prepared by the reaction of a Formula 1A compound with iodine. The reaction is carried out in a polar organic solvent, such as methanol, or a mixture of a polar organic solvent and water, such as aqueous methanol. When the reaction is carried out in aqueous methanol, a buffer may be added to the solvent mixture. A preferred buffer is sodium acetate. The reaction is preferably carried out at a temperature from about 30° C. to about 70° C. for about 2 to about 6 hours.

The di-N-demethyl derivatives, the Formula 1C compounds, may be prepared by the reaction of a Formula 1A and Formula 1B compound with sodium methoxide/iodine. The reaction is preferably carried out in a polar organic solvent, such as methanol. Further, the reaction is carried out at a temperature from about 10° C. to about 15° C., preferably between 0° C. to 5° C. The reaction times vary from about 4 hours to about 6 hours.

Illustrative examples of the Formula 1B and 1C compounds are shown in the following formula:

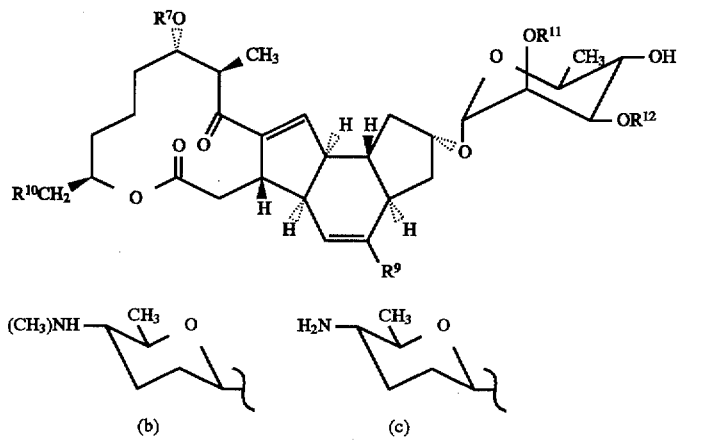

wherein $R^7$, $R^9$, $R^{10}$, $R^{11}$ and $R^{12}$ are for each compound as

| Compound | $R^7$ | $R^9$ | $R^{10}$ | $R^{11}$ | $R^{12}$ |
|---|---|---|---|---|---|
| N-demethyl-A83543K | (b) | H | $CH_3$ | $CH_3$ | $CH_3$ |
| di-N-demethyl-A83543K | (c) | H | $CH_3$ | $CH_3$ | $CH_3$ |
| N-demethyl-A83543O | (b) | $CH_3$ | $CH_3$ | $CH_3$ | $CH_3$ |
| di-N-demethyl-A83543O | (c) | $CH_3$ | $CH_3$ | $CH_3$ | $CH_3$ |
| N-demethyl-A83543P | (b) | H | $CH_3$ | $CH_3$ | H |
| di-N-demethyl-A83543P | (c) | H | $CH_3$ | $CH_3$ | H |
| N-demethyl-A83543U | (b) | H | $CH_3$ | H | $CH_3$ |
| di-N-demethyl-A83543U | (c) | H | $CH_3$ | H | $CH_3$ |
| N-demethyl-A83543V | (b) | $CH_3$ | $CH_3$ | H | $CH_3$ |
| di-N-demethyl-A83543V | (c) | $CH_3$ | $CH_3$ | H | $CH_3$ |
| N-demethyl-A83543W | (b) | $CH_3$ | $CH_3$ | $CH_3$ | H |
| di-N-demethyl-A83543W | (c) | $CH_3$ | $CH_3$ | $CH_3$ | H |
| N-demethyl-A83543Y | (b) | H | H | $CH_3$ | $CH_3$ |
| di-N-demethyl-A83543Y | (c) | H | H | $CH_3$ | $CH_3$ |

The Formula 2 compounds, which are the Formula 1 compounds wherein $R^7$ is other than hydrogen, can react to form various salts, which are also a part of this invention. These salts are useful, for example, in separating and purifying the Formula 2 compounds. In addition, some of the salt forms may have increased water solubility. These salts are prepared using standard procedures for salt preparation. For example, A83543K can be neutralized with an appropriate acid to form an acid addition salt.

The acid addition salts are particularly useful. Representative suitable salts include those salts formed by standard reactions with both organic and inorganic acids such as, for example, sulfuric, hydrochloric, phosphoric, acetic, succinic, citric, lactic, maelic, fumaric, cholic, pamoic, mucic, glutamic, camphoric, glutaric, glycolic, phthalic, tartaric, formic, lauric, stearic, salicyclic, methanesulfonic, benzenesulfonic, sorbic, picric, benzoic, cinnamic, and like acids.

For convenience in the discussions which follow, A83543A-producing strains have been given the following designations: A83543.1, A83543.3, A83543.4, and A83543.5. Also, a new A83543K-producing strain has been given the designation A83543.8. Cultures A83543.1, A83543.3, A83543.4, A83543.5, A83543.6, A83543.7, A83543.8 and A83543.9 have been deposited and made a part of the stock culture collection of the Midwest Area Regional Research Center, Agricultural Research Service, United States Department of Agriculture, from which they are available to the public under the following accession numbers:

| NRRL No. | Strain No. |
|---|---|
| 18395 | A83543.1 |
| 18537 | A83543.3 |
| 18538 | A83543.4 |
| 18539 | A83543.5 |
| 18719 | A83543.6 |

| NRRL No. | Strain No. |
|---|---|
| 18720 | A83543.7 |
| 18743 | A83543.8 |
| 18823 | A83543.9 |

Culture A83543.1 was obtained by chemical mutation of culture A83543, which was isolated from a soil sample collected in the Virgin Islands. Mertz and Yao (1990), *Int'l J. of Systematic Bacteriology*, 48:34. Culture 83543.4 was derived from culture A83543.1. Each of the strains A83543.3, A83543.4, A83543.5, A83543.6, and A83543.7 was derived from A83543.1 by chemically-induced mutagenesis with N-methyl-N'-nitro-N-nitrosoguanidine. Strains A83543.8 and A83543.9 were derived from A83453.4 by chemically-induced mutagenesis with N-methyl-N'-nitro-N-nitrosoguanidine. Except for differences in the production of the A83543 components, these isolates appear the same as the parent culture.

Cultural Characteristics

Cultures A83543.1, A83543.3, A83543.4, A83543.5, A83543.6, A83543.7, A83543.8 and A83543.9 were grown on twelve agar plating media and compared for growth, reverse color, aerial hyphae production, spore mass color, and soluble pigment production. No significant differences were observed on any of the media used. The cultures grew well on both complex and defined media. Aerial hyphae were produced on most of the media used. The aerial spore mass color was predominantly white, and the reverse side was yellow to yellow-brown. No distinctive pigmentation was present; however, a soluble brown pigment was released into some media. The cultural characteristics of A83543.3, A83543.4, A83543.5, A83543.6, A83543.7, A83543.8, and A83543.9 are similar to the original taxonomic description of A83543.1 (see Mertz and Yao (1990), supra).

Morphological Characteristics

Well-formed aerial hyphae, which were segmented into long chains of spores arranged as hooks and open loops, were present on most of the media. Spirals were also observed, but they were short and incomplete. The general morphology was rectus-flexibilis. Aerial hyphae of each of the strains had a distinctive bead-like appearance, with many empty spaces in the spore chain. This feature demonstrated that a spore sheath encased the spore chain, which is a distinctive feature of the genus Saccharopolyspora. Except for differences in the production of the A83543 components, these isolates appear similar to the parent culture.

Physiological Characteristics

Fatty acid analyses from each of the strains were compared. Cells were grown for 96 hours at 28° C. in trypticase soy broth (Difco Laboratories, Detroit, Mich.). Fatty acid methyl esters were analyzed by gas-liquid chromatography with a model 5898A computer-controlled gas-liquid chromatography system (Hewlett-Packard Co., Palo Alto, Calif.) (see Miller and Berger, "Bacterial Identification by Gas Chromatography of Whole Cell Fatty Acids," Hewlett-Packard Application Note 228–41. These results are presented in Table VIII).

TABLE VIII

| Fatty Acid | A.83543.1 | A83543.3 | A83543.4 | A83543.5 | A83543.6 | A83543.7 | A83543.8 | A83543.9 |
|---|---|---|---|---|---|---|---|---|
| 15:0 ISO | 15.95 | | 22.47 | | 16.49 | 17.00 | 19.76 | 17.42 |
| 16:0 ISO | 28.71 | | 22.00 | | 25.76 | 27.39 | 23.14 | 24.34 |
| 16:1 Cis 9 | — | | 1.35 | | — | — | 0.90 | 0.92 |
| 15:0 ISO 2OH | 2.67 | | 2.02 | | 3.87 | 3.95 | 2.44 | 1.78 |
| 16:0 | 1.20 | | 0.69 | | 0.63 | 0.60 | 0.47 | 0.36 |
| 17:1 ISO F[1] | 5.52 | | 8.62 | | 7.54 | 5.51 | 7.55 | 8.72 |
| 17:0 Iso | :13.55 | | 20.67 | | 16.40 | 13.89 | 21.15 | 19.43 |
| 17:0 Anteiso | 8.39 | | 3.94 | | 4.69 | 5.18 | 3.57 | 5.52 |
| 17:1 B | 4.14 | | 3.97 | | 4.65 | 6.68 | 4.47 | 4.61 |
| 17:1 C | 2.52 | | 2.88 | | 4.90 | 5.53 | 3.18 | 3.02 |
| 17:0 | 4.26 | | 1.49 | | 3.13 | 3.84 | 2.25 | 1.67 |
| 16:1 2OH | 1.87 | | 1.52 | | 1.93 | 0.92 | 1.36 | 2.17 |
| 18:1 Iso F | 6.55 | | 4.16 | | 5.82 | 6.00 | 5.75 | 5.74 |
| 18:1 Cis 9 | 0.34 | | 1.03 | | 0.64 | 0.63 | 0.96 | 0.84 |

[1]F, B and C indicate double bond positions or configuration that are unknown.

Figure 13:
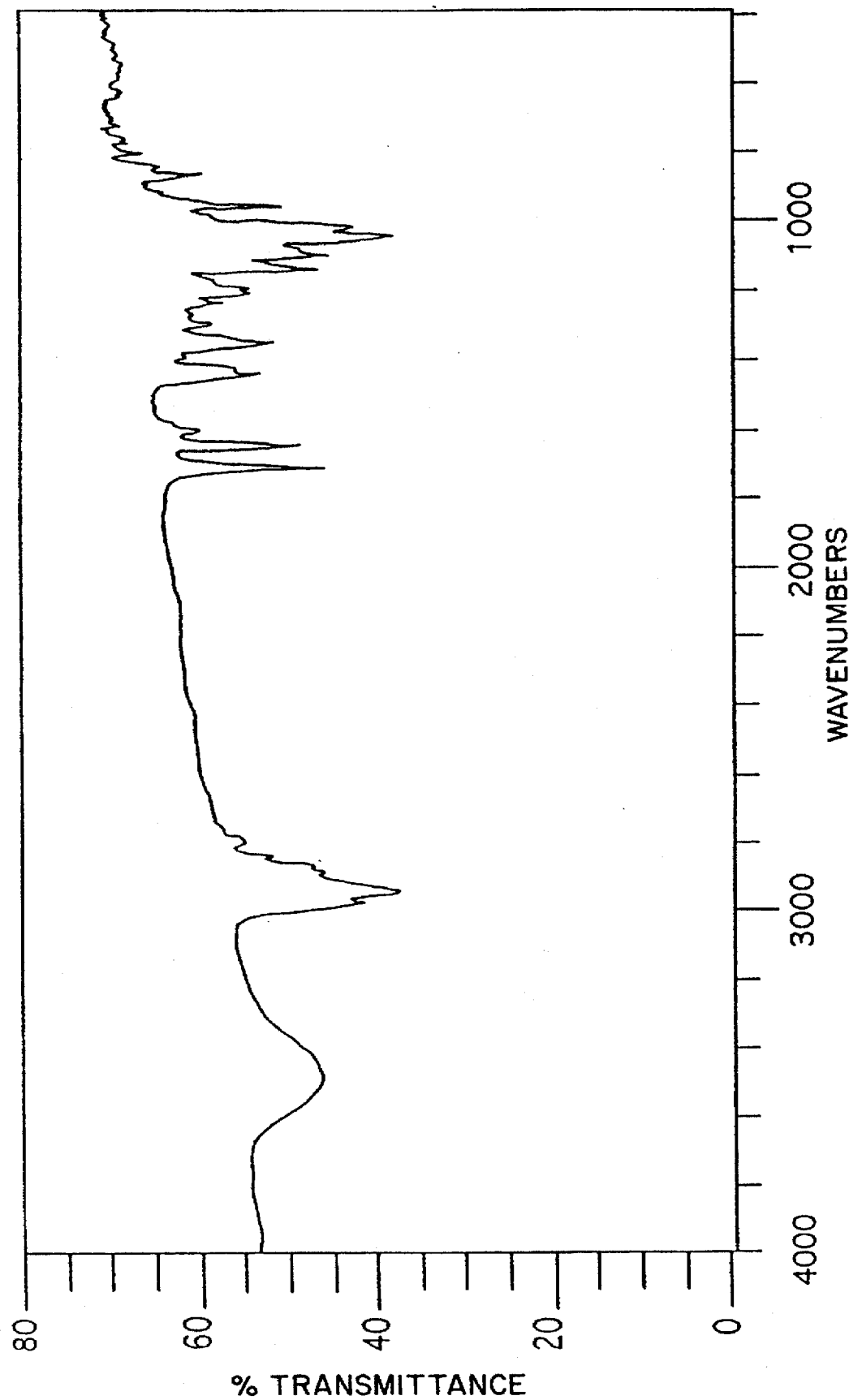
FIG. 13 shows the infrared absorption spectrum of A83543V in KBr.
Figure 14:
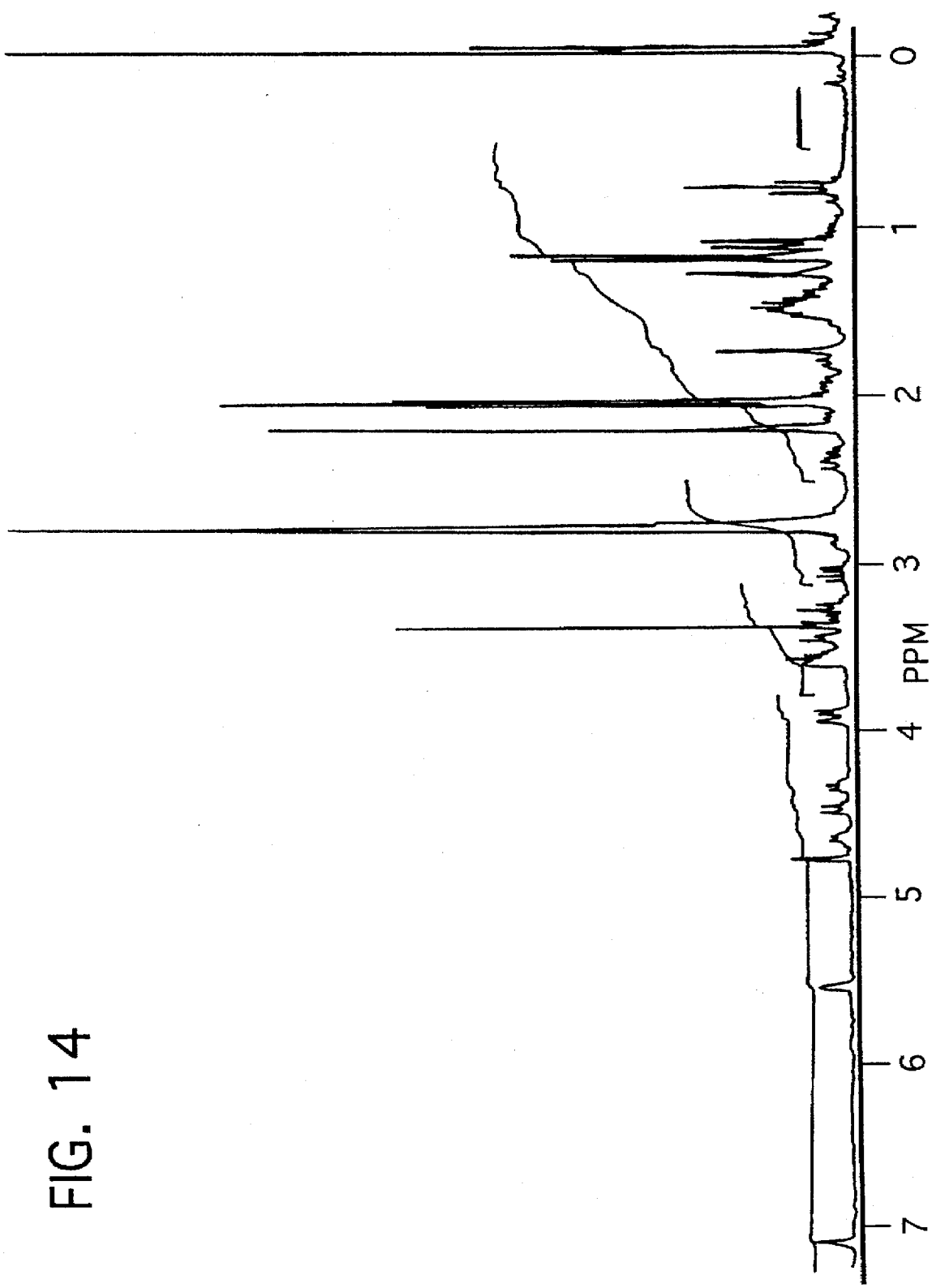
FIG. 14 shows the proton nuclear magnetic resonance spectrum of A83543V in acetone-$d_6$.
Figure 15:
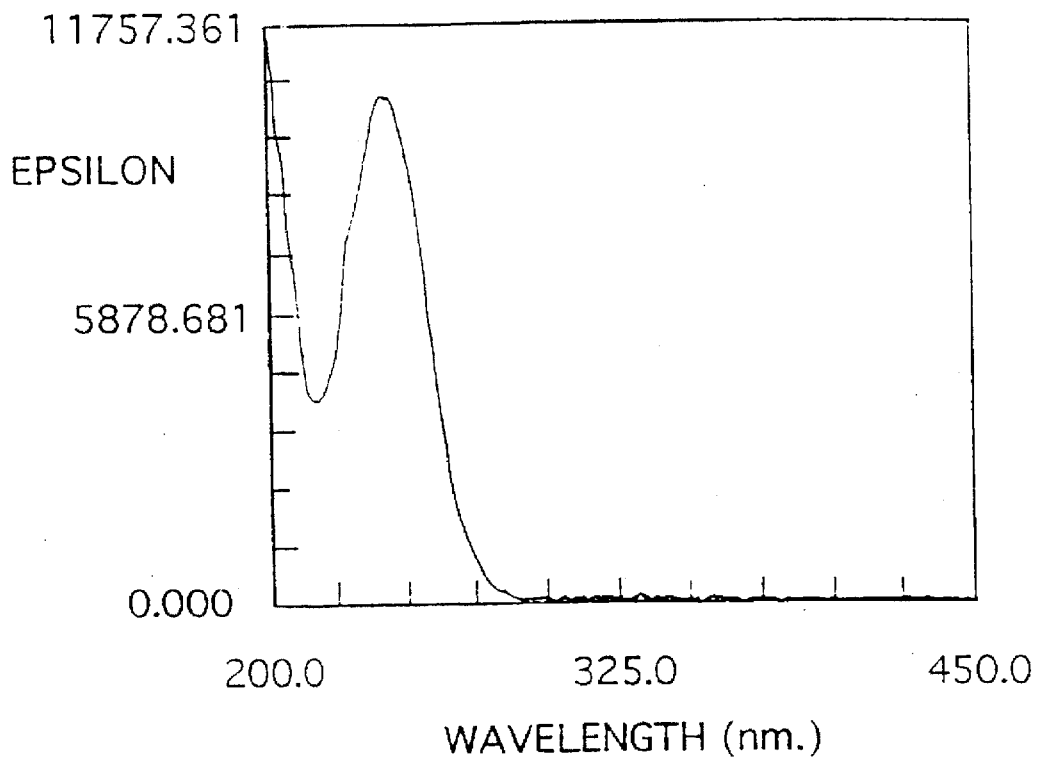
FIG. 15 shows the UV spectrum spectrum of A83543V in EtOH.
Figure 18:
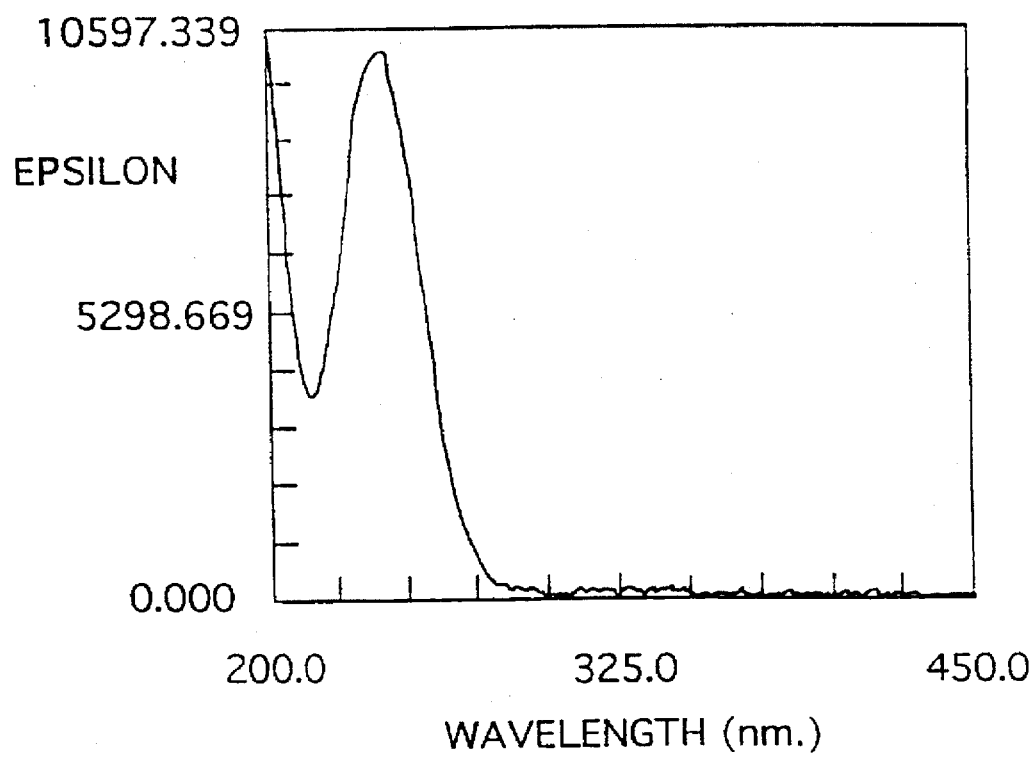
FIG. 18 shows the UV spectrum spectrum of A83543W in EtOH.
Figure 16:
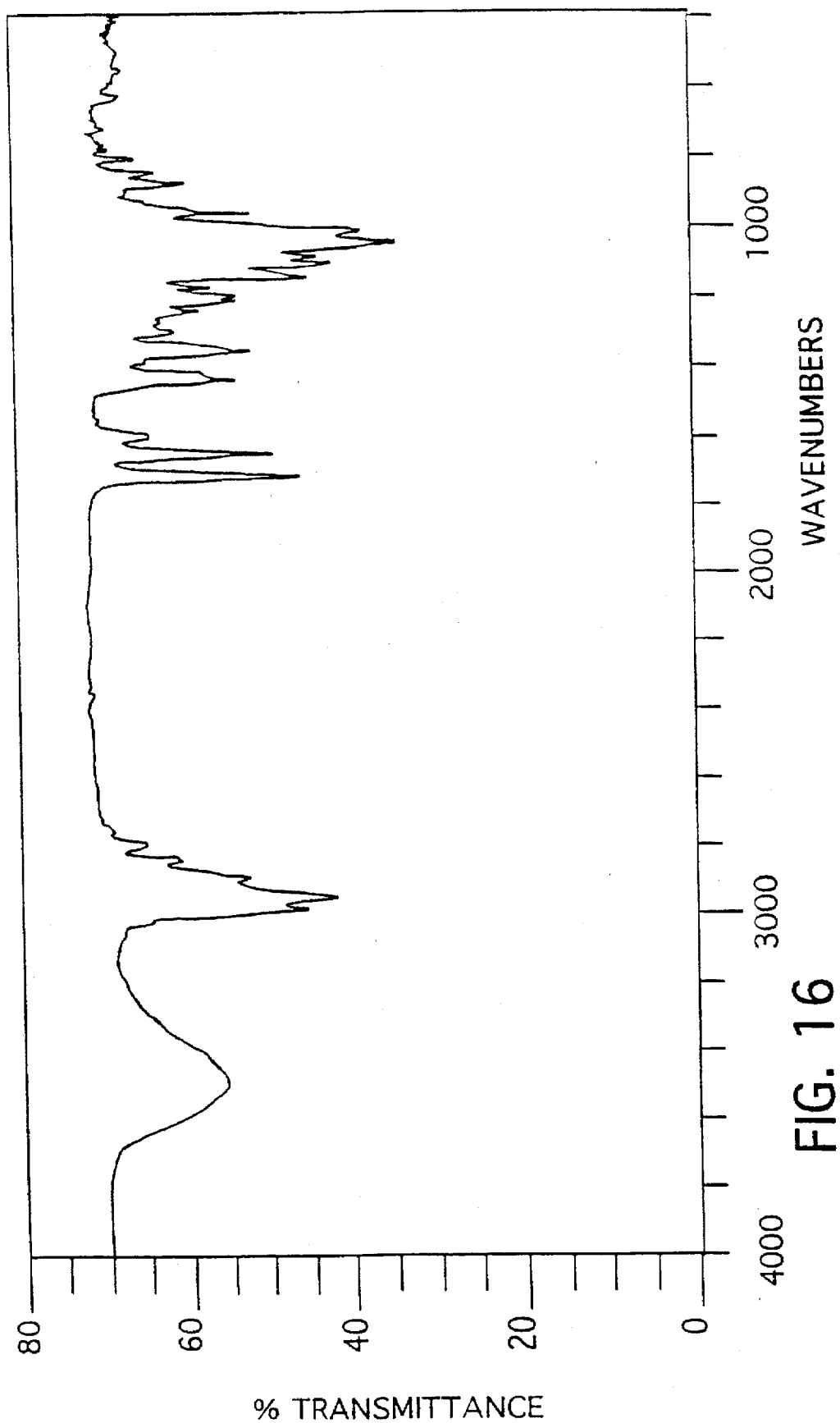
FIG. 16 shows the infrared absorption spectrum of A83543W in KBr.
Figure 17:
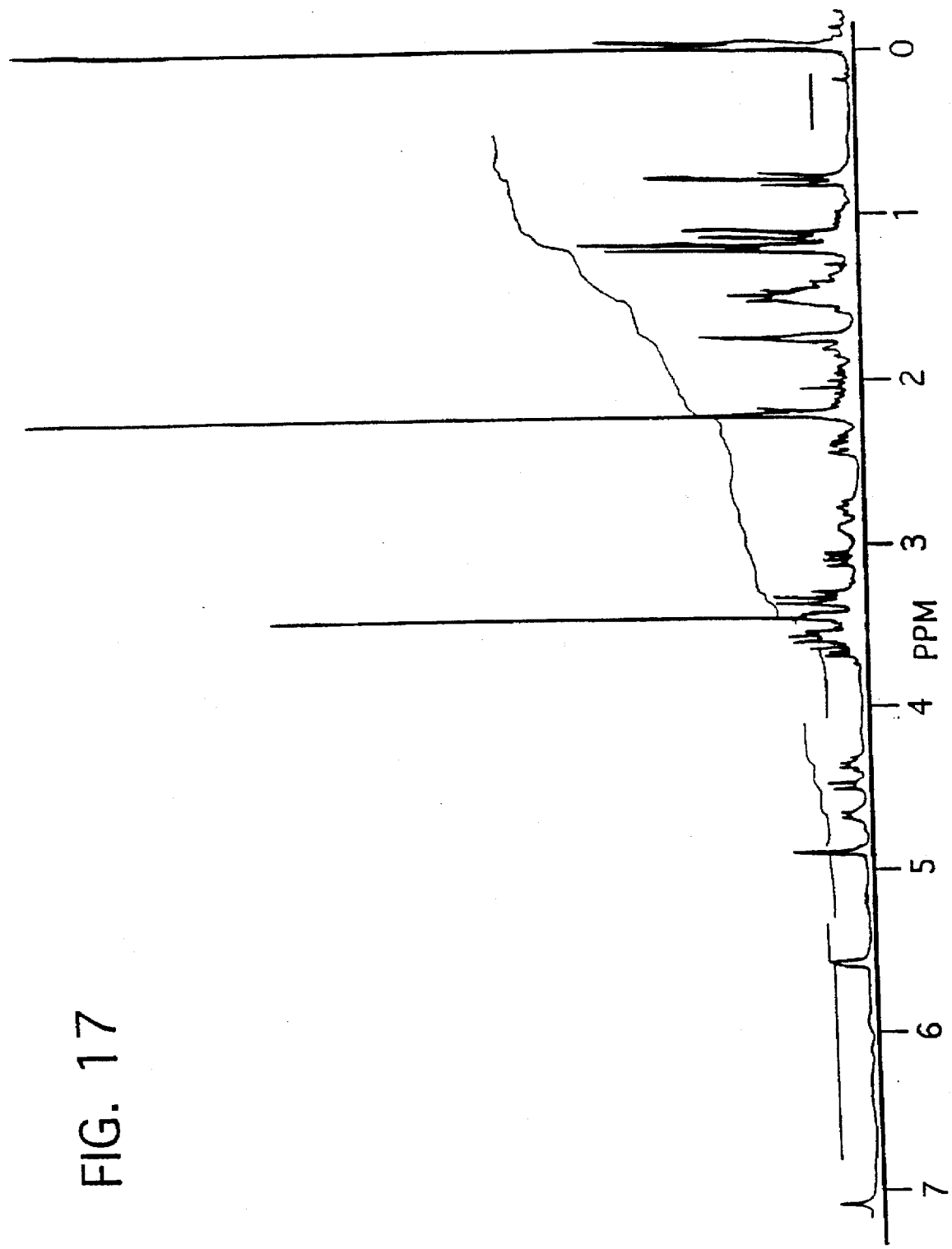
FIG. 17 shows the proton nuclear magnetic resonance spectrum of A83543W in acetone-$d_6$.
Figure 19:
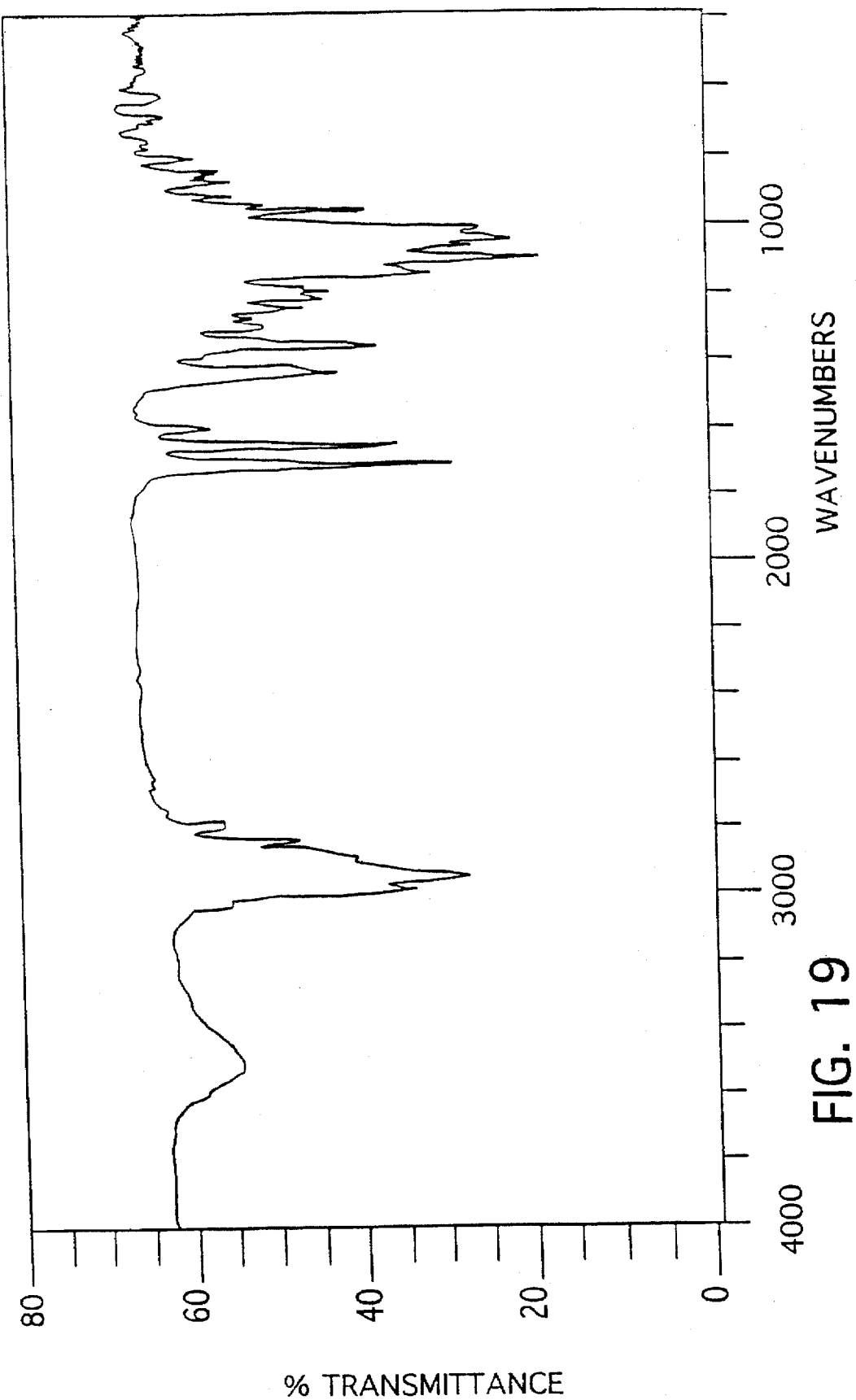
FIG. 19 shows the infrared absorption spectrum of A83543Y in KBr.
Figure 20:
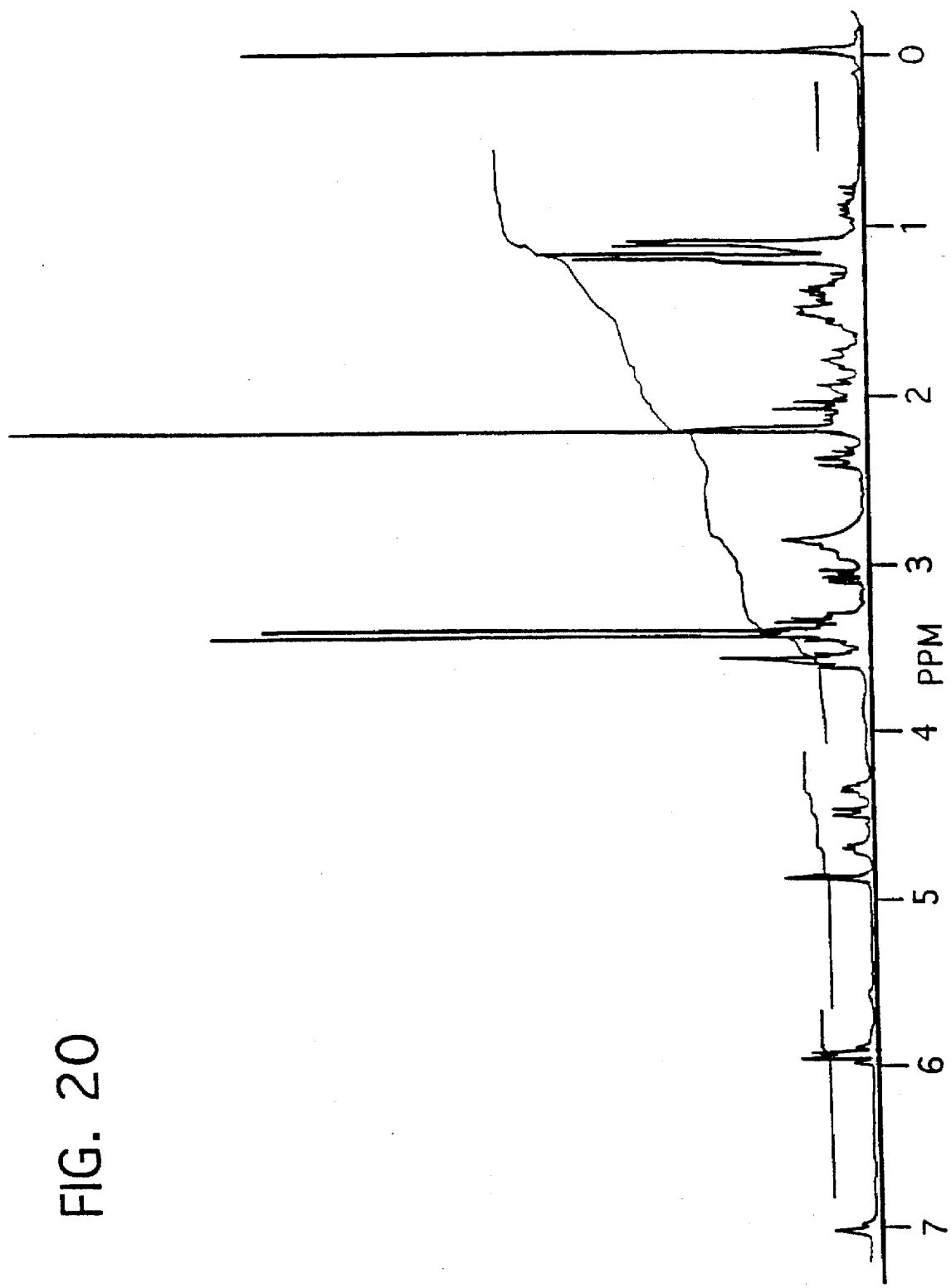
FIG. 20 shows the proton nuclear magnetic resonance spectrum of A83543Y in acetone-$d_6$.
Figure 21:
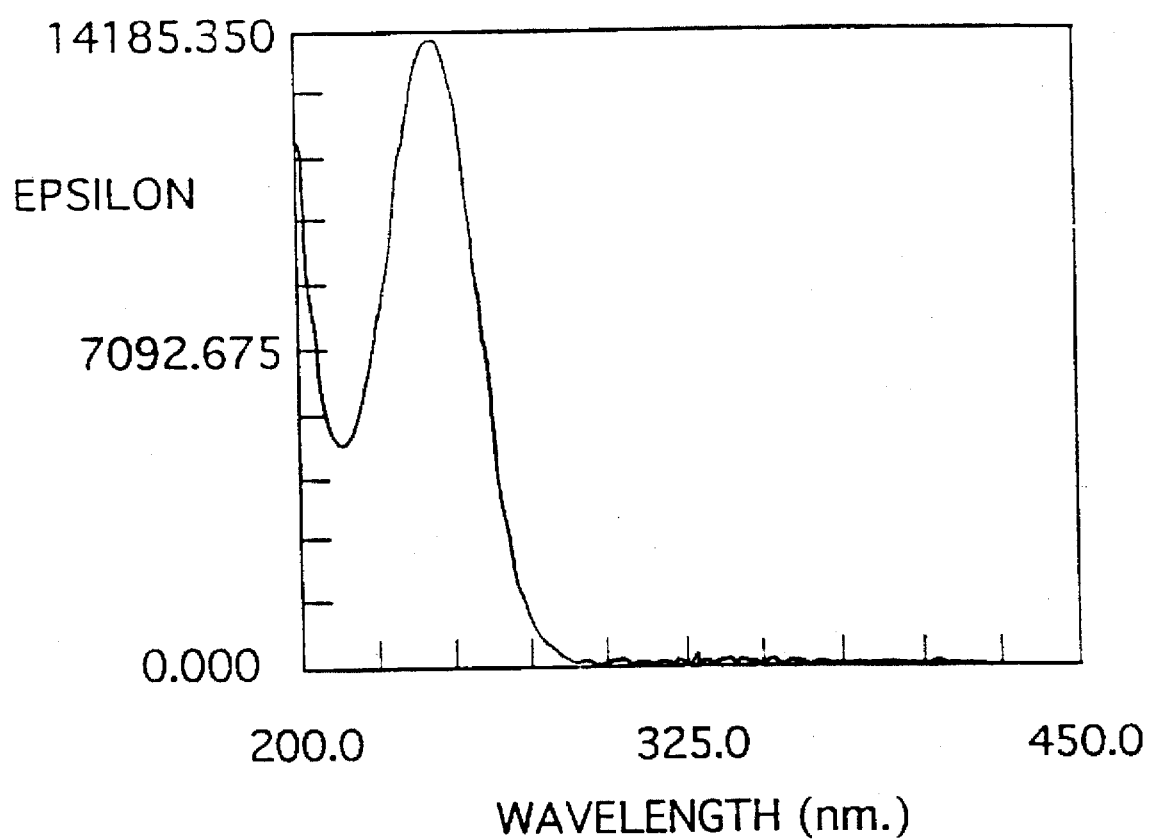
FIG. 21 shows the UV spectrum spectrum of A83543Y in EtOH.
Figure 22:
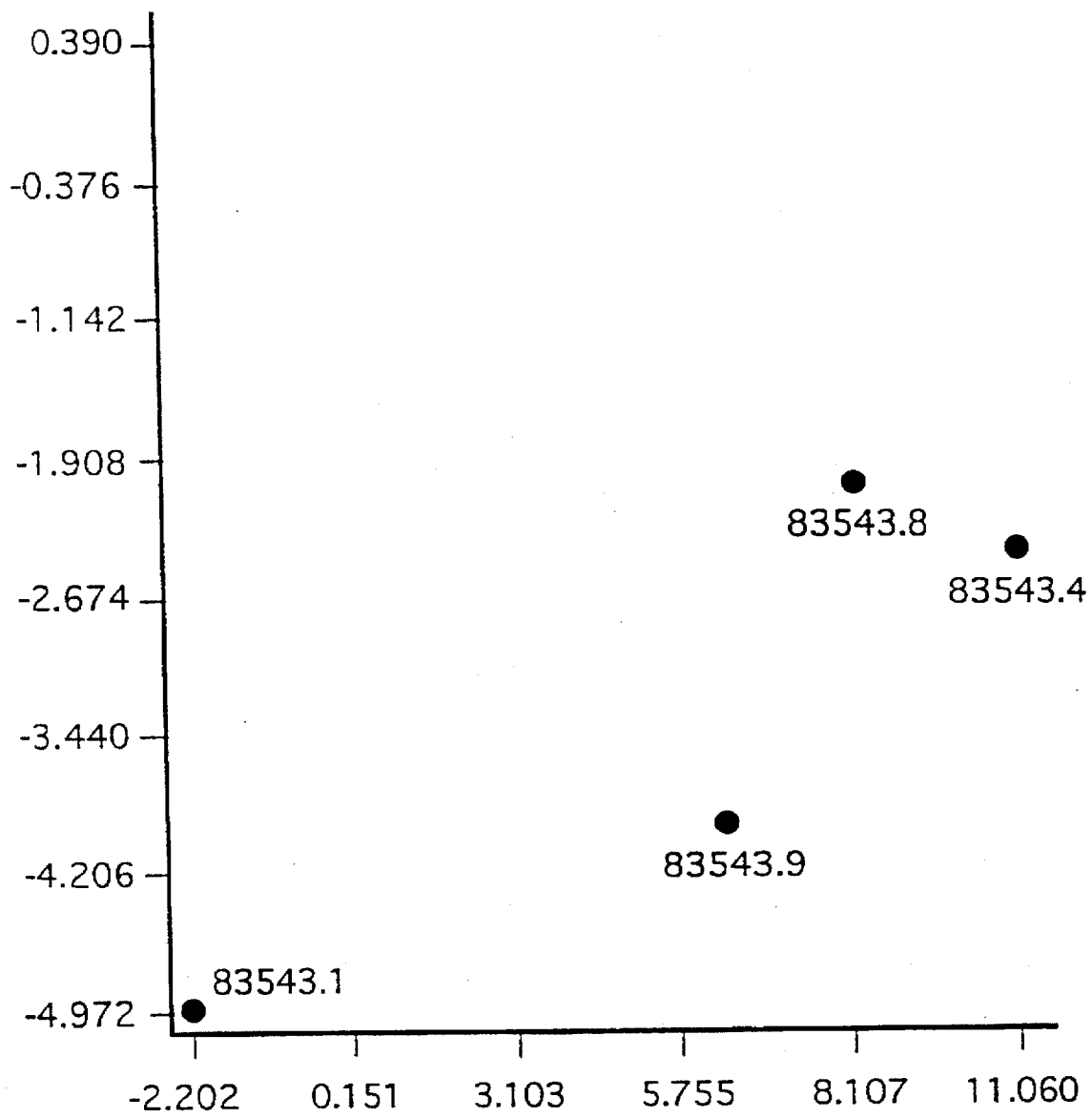
FIG. 22 shows the principle component plot of fatty acid analyses for strains A83543.1, A83543.3, A83543.4, A83543.5, A83543.6, A83543.7, A83543.8 and A83543.9.

Principal-component analysis is a branch of multivariate statistics that deals with internal relationships of a set of variables. In this analysis, the greatest amount of variance within the original data or test results is expressed as principal components (see Alderson, "The Application and Relevance of Nonheirarchic Methods in Bacterial Taxonomy", in Computer-Assisted Bacterial Systematics 227 (1985)). A plot showing scatter or variability can be constructed. Relationships can be evaluated by examining the variance, and a microbial population characterized. A two-dimensional principal component plot from the fatty acid analyses of strains A83543.1, A83543.3, A83543.4, A83543.5, A83543.6, A83543.7, A83543.8 and A83543.9 is shown in FIG. 13. The values refer to the degrees of separation between the strains involved. The differences between the strains are not taxonomically significant.

As is the case with other organisms, the characteristics of the A83543-producing strains are subject to variation. Thus, mutants of these strains may be obtained by physical and chemical methods known in the art. For example, other strains may be obtained by treatment with chemicals such as N-methyl-N'-nitro-N-nitrosoguanidine. Natural and induced mutants of the *S. spinosa* NRRL 18395, NRRL 18537, NRRL 18538, NRRL 18539 NRRL 18719, NRRL 18720, NRRL 18743 and NRRL 18823 strains, which retain the characteristic of producing recoverable amounts of a Formula 1 compound, when cultured in appropriate conditions are applicable in the present invention.

One aspect of the present invention is the production of a compound of Formula 1 produced by culturing an A83543A-producing strain of *S. spinosa* in a suitable culture medium containing sinefungin, selected from the group consisting of NRRL 18395, NRRL 18537, NRRL 18538, and NRRL 18539 or an A83543A-producing mutant thereof. An "A83543A-producing mutant" is a strain derived from any one of the A83543A-producing strains of *S. spinosa*, NRRL 18395, NRRL 18537, NRRL 18538, NRRL 18539, which is capable of producing recoverable amounts of A83543A and which is capable, when cultured in a suitable culture medium containing sinefungin, to produce concomitant amounts of A83543K and A83543O.

Another aspect of the present invention is the production of a compound of Formula 1 by culturing an A83543H-producing strain of *S. spinosa*, such as NRRL 18823 or an A83543H-producing mutant thereof, in a suitable culture medium containing sinefungin. An "A83543H-producing mutant" is a strain derived from any one of the A83543H-producing strains of *S. spinosa*, NRRL 18823, which is capable of producing recoverable amounts of A83543H and which is capable, when cultured in a suitable culture medium containing sinefungin, to produce concomitant amounts of A83543U and A83543V.

A still further aspect of this invention is the production of a compound of Formula 1 by culturing an A83543J-producing strain of *S. spinosa*, such as NRRL 18719 or an A83543J-producing mutant thereof, in a suitable culture medium containing sinefungin. An "A83543J-producing mutant" is a strain derived from any one of the A83543J-producing strains of *S. spinosa*, NRRL 18719 or NRRL 18720, which is capable of producing recoverable amounts of A83543J and which is capable, when cultured in a suitable culture medium containing from about 50 µg/ml to about 200 µg/ml of sinefungin, to produce concomitant amounts of A83543P and A83543W.

Typically, sinefungin is added to the production medium after 48-72 hours or for large scale production, the addition of sinefungin is postponed until the culture begins to grow as indicated by the uptake of oxygen. Preferably, sinefungin is added to the fermentation medium about 48 hours to about 72 hours after inoculation. Sinefungin may be added as a solid or as a solution. For convenience, when sinefungin is added to a large scale fermentation, addition as an alcoholic solution is preferred. Such a solution is prepared by dissolving sinefungin in a sufficient volume of methyl alcohol, then sterilizing the solution by filtration through a 0.45 µ filter.

Alternatively, the Formula 1 compounds are produced by culturing *S. spinosa* strain NRRL 18743 (which produces components A83543K, A83543O and A83543Y), or an A83543K-producing mutant thereof, in a suitable culture medium without the addition of sinefungin. An "A83543K-producing mutant" is a strain derived from *S. spinosa* NRRL 18743 which is capable of producing recoverable amounts of A83543K.

After production, the Formula 1 compound may be separated from the culture medium using various isolation and purification procedures which are well understood in the art. For economy in production, optimal yield, and ease of product isolation, certain culture media are preferred. For example, preferred carbon sources in large-scale fermentation are glucose and methyl oleate, although ribose, xylose, fructose, galactose, mannose, mannitol, soluble starch, potato dextrin, oils such as soybean oil and the like can also be used. Preferred nitrogen sources are cottonseed flour, peptonized milk and corn steep liquor, although fish meal, digested soybean meal, yeast extract, enzyme-hydrolyzed casein, beef extract, and the like can also be used. Among the nutrient inorganic salts which can be incorporated in the culture media are the customary soluble salts capable of yielding zinc, sodium, magnesium, calcium, ammonium, chloride, carbonate, sulfate, nitrate and like ions. Essential trace elements necessary for the growth and development of the organism should also be included in the culture medium. Such trace elements commonly occur as impurities in other substituents of the medium in amounts sufficient to meet the growth requirements of the organism.

Usually, if foaming is a problem, small amounts (i.e., 0.2 ml/L) of an antifoam agent such as polypropylene glycol may be added to large-scale fermentation media. In the case of the A83543-producing cultures, however, conventional defoamers inhibit A83543 production. Foaming can be controlled by including soybean oil or PLURONIC L-101 (BASF, Parsippany, N.J.) in the medium (1-3%). Additional oil may be added if foaming develops.

For production of substantial quantities of a Formula 1 compound, submerged aerobic fermentation in stirred bioreactors is preferred; however, small quantities of a Formula 1 compound may be obtained by shake-flask culture. Because of the time lag in production commonly associated with inoculation of large bioreactors with the spore form of the organism, it is preferable to use a vegetative inoculum. The vegetative inoculum is prepared by inoculating a small volume of culture medium from a stock culture preserved in liquid nitrogen to obtain a fresh, actively growing culture of the organism. The vegetative inoculum is then transferred to a larger bioreactor. The vegetative inoculum medium can be the same as that used for larger fermentations, but other media are also suitable.

The Formula 1 compound is produced by the A83543-producing strains when grown at temperatures between about 24° C. and about 33° C. Optimum temperatures for production appear to be about 28°-30° C.

As is customary in submerged aerobic culture processes, sterile air is blown into the vessel from the bottom while the medium is stirred with conventional turbine impellers. In general, the aeration rate and agitation rate should be sufficient to maintain the level of dissolved oxygen at or above 80%, with an internal vessel pressure of about 0.34 atmospheres.

Production of the Formula 1 compound can be followed during the fermentation by testing extracts of the broth. A preferred method for following the production is analysis of the broth extracts by high performance liquid chromatography (HPLC). A suitable system for analysis is described in Example 1.

Following the production in shake flasks or in stirred reactors, the Formula 1 compound can be recovered from the fermentation medium by methods used in the art. The compounds produced during fermentation of the A83543-producing strain occur in both the mycelia and the broth. The Formula 1 compounds are lipophilic; when a substantial amount of oil is used in the fermentation, whole broth extraction is more efficient. If only small amounts of oil are used, the major portion of the Formula 1 compound is present in the mycelia. In that case, more efficient recovery of the Formula 1 compound is accomplished by initially filtering the medium to separate the broth from the mycelial mass (the biomass).

The Formula 1 compound can be recovered from the biomass by a variety of techniques. A suitable technique involves washing the separated biomass with water to remove remaining broth, mixing the biomass with a polar solvent in which the Formula 1 compound is soluble, e.g., methanol or acetone, separating and concentrating the solvent, extracting the concentrate with a non-polar solvent and/or adsorbing it onto a reverse-phase silica gel adsorbent, such as reverse phase $C_8$ or $C_{18}$ resin, or a high porous polymer such as HP-20 or HP-20ss (Mitsubishi Chemical Industries Co., Ltd., Japan). The active material is eluted from the adsorbent with a suitable solvent such as, for example, $H_2O$:acetonitrile:methanol mixtures, optionally containing small amounts of THF.

A preferred technique for isolating the Formula 1 compound from the biomass involves adding an equal volume of acetone to the whole broth, filtering the mixture in a ceramic filter to remove the biomass, and extracting the filtrate with ethyl acetate. The ethyl acetate extract is concentrated in vacuo to remove the acetone, and the aqueous layer is separated from the organic layer. The ethyl acetate solution is further concentrated in vacuo, and the concentrate is extracted with dilute aqueous acid (pH 3). The Formula 1 compound may be further purified by chromatography as described herein.

A more preferred technique for isolating the Formula 1 compound from the biomass involves adding an equal volume of acetone to the whole broth, filtering the mixture in a ceramic filter to remove the biomass, and adjusting the pH of the filtrate to about pH 9 to about pH 13. This solution is applied to HP-20ss (Mitsubishi Chemical Industries Co., Ltd., Japan) and the column washed with a mixture of methanol, acetonitrile, and water (1:1:2). The Formula 1 compound is eluted with a 95:5 mixture of methanol/acetonitrile (1:1) containing 0.1% ammonium acetate (pH 8.1). The fractions containing the Formula 1 compounds are combined and lyophilized. The Formula 1 compound may be further purified by chromatography as described herein.

Alternatively, the culture solids, including medium constituents and mycelium, can be used without extraction or separation, but preferably after removal of water, as a source of the Formula 1 compound. For example, after production of the Formula 1 compound, the whole fermentation broth can be dried by lyophilization, by drum-drying, or by azeotropic distillation and drying. The dried broth can then be used directly, for example, by mixing it directly into feed premix or into formulations for sprays and powders.

Insecticide and Miticide Activity

The Formula 2 compounds are useful for the control of insects and mites. Therefore, a further aspect of the present invention is directed to methods for inhibiting an insect or mite which comprises applying to the locus of the mite or insect an insect- or mite-inhibiting amount of a Formula 2 compound.

The "locus" of the insect or mite refers to the environment in which the insect or mite lives or where its eggs are present, including the air surrounding it, the food it eats, or objects which it contacts. For example, plant-ingesting insects or mites can be controlled by applying the active compound to plant parts which the insects or mites eat or inhabit, particularly the foliage.

The term "inhibiting an insect or mite" refers to a decrease in the number of living insects or mites or to a decrease in the number of viable insect or mite eggs. The extent of reduction accomplished by a compound depends, of course, upon the application rate of the compound, the particular compound used, and the target insect or mite species. At least an insect-inactivating or mite-inactivating amount should be used.

The terms "insect-inactivating amount" and "mite-inactivating amount" are used to describe the amount which is sufficient to cause a measurable reduction in the treated insect or mite population. Generally, an amount in the range from about 1 to about 1,000 ppm (or 0.01 to 1 kg/a) of active compound is used.

The Formula 2 compounds show activity against a number of insects and mites. More specifically, the compounds show activity against beet armyworm and tobacco budworm, which are members of the insect order Lepidoptera. Other typical members of this order are southern armyworm, codling moth, cutworms, clothes moths, Indian meal moth, leaf rollers, corn ear worm, cotton bollworm, European corn borer, imported cabbage worm, cabbage looper, pink bollworm, bagworms, Eastern tent caterpillar, sod webworm, and fall armyworm.

The Formula 2 compounds also show activity against leaf hoppers, which is a member of the insect order Homoptera. Other members of this order include cotton aphid, plant hoppers, pear psylla, apple sucker, scale insects, whiteflies, and spittle bugs, as well as a number of other host-specific aphid species.

In addition, the Formula 2 compounds show activity against stable flies, blowflies, and mosquitoes, which are members of the insect order Diptera. Another typical member of this order is the common house fly.

The Formula 2 compounds also show activity against two-spotted spider mites, which is a member of the insect order Acarina. Other typical members of this order include mange mite, scab mite, sheep scab mite, chicken mite, scalyleg mite, deplumbing mite, and dog follicle mite.

The Formula 2 compounds are useful for reducing populations of insects and mites and are used in a method of inhibiting an insect or mite population which comprises applying to a locus of the insect or mite an effective insect- or mite-inactivating amount of a Formula 2 compound. In one preferred embodiment, the present invention is directed to a method for inhibiting a susceptible insect of the order Lepidoptera which comprises applying to a plant an effective insect-inactivating amount of a Formula 2 compound in accordance with the present invention. Another preferred embodiment of the invention is directed to a method of inhibiting biting flies of the order Diptera in animals which comprises administering an effective pest-inhibiting amount of a Formula 2 compound orally, parenterally, or topically to the animal. In another preferred embodiment, the present invention is directed to a method for inhibiting a susceptible insect of the order Homoptera which comprises applying to a plant an effective insect-inactivating amount of a Formula 2 compound. Another preferred embodiment of the invention is directed to a method of inhibiting mites of the order Acarina which comprises applying to the locus of the mite a mite-inactivating amount of a Formula 2 compound.

Mite/Insect Screen

The Formula 2 compounds were tested for miticidal and insecticidal activity in the following mite/insect screen. Each test compound was formulated by dissolving the compound in an acetone-alcohol (1:1) mixture containing 23 g of TOXIMUL R (sulfonate/nonionic emulsifier blend) and 13 g of TOXIMUL S (sulfonate/nonionic emulsifier blend) per liter. These mixtures were then diluted with water to give the indicated concentrations.

Two-spotted spider mites and cotton aphids were introduced on squash cotyledons and allowed to establish on both leaf surfaces. The leaves were then sprayed with 5 ml of test solutions using a DeVilbiss atomizing sprayer at 10 psi. Both surfaces of the leaves were covered until run off and then allowed to dry for one hour. After standard exposure periods percent mortality was evaluated. Additional insects were evaluated using similar formulations and evaluation procedures. The results are reported in Table IX. The following abbreviations are used:

| Abbreviation | Pest | Scientific Name |
|---|---|---|
| ALH | Aster Leafhopper | *Macrosteles fascifrons* |
| BAW | Beet Armyworm | *Spodoptera exiqua* |
| CA | Cotton Aphid | *Aphis gossypiii Glover* |
| GECR | German Cockroach | *Blattella germanica* |
| NEM | Rootknot Nematode | *Meliiodyne spp.* |
| SCRW | Southern Corn Rootworm | *Diabrotica undecimpunctata howardi* |
| TBW | Tobacco Budworm | *Heliothis virescens* |
| TSSM | Two-spotted Spider Mite | *Tetranychus urticae* |

TABLE IX

Activity of Formula 2 Compounds in Insect/Mite Screen

| Pest | rate[a] | per[c] | % Inhibition[b] | | | | | | |
|---|---|---|---|---|---|---|---|---|---|
| | | | A83543K | A83543O | A83543P | A83543U | A83543W | A83543Y | N-demethyl-K |
| ALH | 200 | 24 hr | 100 | 100 | 0 | 100 | 0 | 60 | 100 |
| | 400 | 24/hr | 100 | 100 | 0 | 100 | 0 | 80 | 100 |
| BAW | 200 | 6 day | 100 | 100 | 100 | 100 | 0 | 80 | 100 |
| | 400 | 6 day | 100 | 100 | 100 | 100 | 60 | 100 | 100 |
| CA | 200 | 4–5 day | 0 | 0 | 0 | 0 | 0 | 0 | 0 |
| | 400 | 4–5 day | 0 | 100 | 0 | 0 | 0 | 0 | 0 |
| GECR | 200 | 7 day | 0 | 0 | 0 | 0 | 0 | 0 | 0 |
| | 400 | 7 day | 0 | 0 | 0 | 0 | 0 | 0 | 0 |
| | 200 | 21 day | 0 | 20 | 20 | 0 | 20 | — | 20 |
| | 400 | 21 day | 80 | 100 | 0 | 0 | 0 | — | 60 |
| NEM | 200 | 11 day | 0 | 0 | 0 | 0 | 0 | — | — |
| | 400 | 11 day | 0 | 0 | 0 | 0 | 0 | — | 100 |
| SCRW | 200 | 11 day | | 0 | 0 | 0 | 0 | 0 | — |
| | 400 | 11 day | 100 | 0 | 0 | 0 | 0 | 0 | 60 |
| TBW | 200 | 6 day | 100 | 100 | 0 (50) | 100 (50) | 0 (50) | 0 (50) | 100 (50) |
| | 400 | 6 day | 100 | 100 | 100 | 100 | 100 | 100 | 100 |
| TSSM | 200 | 4–5 day | 90 | 100 | 100 (50) | 0 | 0 (50) | 0 (50) | 0 (50) |
| | 400 | 4–5 day | 100 | 100 | 100 | 0 | 80 | 100 | 100 |

[a]rate in ppm (unless otherwise indicated in parenthesis)
[b]% inhibition as a mean of single replicate tests
[c]exposure period.

Formula 2 compounds were evaluated in the following assay to determine the $LD_{50}$ against neonate tobacco budworm (*Heliothis virescens*). A petri dish (100 mm×20 mm) is inverted and the lid lined with a #1 qualitative filter paper. Ten neonate larvae are placed in each dish and a 1 ml test solution is pipetted onto the insects. The petri dish bottom is then placed on the lid to contain the larvae. At 1 hour after treatment, a small piece of Heliothis diet (modified slurry, Southland Products, Lake Village, Ariz.) is added to each dish. The mortality is evaluated at 24 and 48 hours. The tests were run in triplicate. The results are shown in Table X.

TABLE X

Activity Against Neonate Tobacco Budworm

| Compound | $LD_{50}$ (ppm)[a] |
|---|---|
| A83543K | 3.5 |
| A83543O | 1.4 |
| A83543P | >64 |
| A83543U | 22 |
| A83543W | >64 |

TABLE X-continued

Activity Against Neonate Tobacco Budworm

| Compound | $LD_{50}$ (ppm)[a] |
|---|---|
| A83543Y | 20 |
| N-de-methyl-K | 9.8 |

[a]mean of two tests

Insecticidal Compositions

The Formula 2 compounds of this invention are applied in the form of compositions, which are also a part of this invention. These compositions comprise an insect- or mite-inactivating amount of a Formula 2 compound in a phytologically acceptable inert carrier. The active component, the Formula 2 compound, may be present as a single Formula 2 compound, a mixture of two or more Formula 2 compounds, a mixture of at least one of A83543K, A83543O, A83543P, A83543U, A83543V, A83543W and A83543Y or a mixture of at least one of A83543K, A83543O, A83543P, A83543U, A83543V, A83543W and A83543Y together with the dried portion of the fermentation medium in which it is produced.

Compositions are prepared according to procedures and formula which are conventional in the agricultural chemical art, but which are novel and important because of the presence of one or more of the compounds of this invention. The compositions are either concentrated formulations which are dispersed in water for application or dust or granular formulations which are applied without further treatment.

The dispersions in which the compound or crude dried material are applied are most often aqueous suspensions or emulsions prepared from concentrated formulations of the compounds or crude material. Such water-soluble, water-suspendible, or emulsifiable formulations are either solids (usually known as wettable powders) or liquids (usually known as emulsifiable concentrates or aqueous suspensions).

Wettable powders, which may be compacted to form water dispersible granules, comprise an intimate mixture of the active compound, an inert carrier, and surfactants. The concentration of the active compound is usually from about 1% to about 90% by weight. The inert carrier is usually chosen from among attapulgite clays, the montmorillonite clays, the diatomaceous earths or the purified silicates.

Effective surfactants, comprising from about 0.5% to about 10% of the wettable powder are found among the sulfonated lignins, the condensed naphthalene-sulfonates, the napthalene-sulfonates, the alkyl-benzenesulfonates, the alkylsulfates, and nonionic surfactants such as ethylene oxide adducts of alkylphenols.

Emulsifiable concentrates of the compounds comprise a convenient concentration of a compound, such as from about 50 to about 500 grams per liter of liquid, equivalent to about 10% to about 50%, dissolved in an inert carrier which is either a water-miscible solvent or mixture of a water-immiscible organic solvent and emulsifiers. Useful organic solvents include aromatics, especially the xylenes, and petroleum fractions, especially high-boiling naphthlenic and olefinic portions of petroleum such as heavy or aromatic naphtha. Other organic solvents may also be used, such as the terpenic solvents, including rosin derivatives, aliphatic ketones such as cyclohexanone, and complex alcohols such as 2-ethoxyethanol. Suitable emulsifiers for emulsifiable concentrates are chosen from conventional nonionic surfactants, such as those mentioned above.

Aqueous suspensions comprise suspensions of water-insoluble compounds of this invention dispersed in an aqueous vehicle at a concentration in the range from about 5% to about 50% by weight. The suspensions are prepared by finely grinding the compound, and vigorously mixing it into a vehicle comprised of water and surfactants chosen from the same types discussed above. Inert ingredients, such as inorganic salts and synthetic or natural gums may also be added to increase the density and viscosity of the aqueous vehicle. It is often most effective to grind and mix the compound at the same time by preparing the aqueous mixture and homogenizing it in an implement such as a sand mill, ball mill, or piston-type homogenizer.

The Formula 2 compounds may also be applied as granular compositions, which are particularly useful for applications to the soil. Granular compositions usually contain from about 0.5% to about 10% by weight of the Formula 2 compound, dispersed in an inert carrier which consists entirely or in large part of clay or a similar inexpensive substance. Such compositions are usually prepared by dissolving the compound in a suitable solvent and applying it to a granular carrier which has been pre-formed to the appropriate particle size in the range of from about 0.5 to 3 mm. Such compositions may also be formulated by making a dough or paste of the carrier, drying the combined mixture of the active ingredient in the dough or paste, and crushing the dried composition to obtain the desired granular particle size.

Dusts containing the compound are prepared by intimately mixing the compound in powdered form with a suitable dust agricultural carrier, such as kaolin clay, ground volcanic rock, and the like. Dusts can suitably contain from about 1% to about 10% of the Formula 2 compound.

It is equally practical, when desirable for any reason, to apply the compound in the form of a solution in an appropriate organic solvent, usually a bland petroleum oil, such as the spray oils, which are widely used in agricultural chemistry.

Insecticides and miticides are usually applied in the form of a dispersion of the active ingredient in a liquid carrier. It is conventional to refer to application rates in terms of the concentration of active ingredient in the carrier. The most widely used carrier is water.

The Formula 2 compounds can also be applied in the form of an aerosol composition. In such compositions the active compound is dissolved in an inert carrier, which is a pressure-generating propellant mixture. The aerosol composition is packaged in a container from which the mixture is dispersed through an atomizing valve. Propellant mixtures comprise either low-boiling halocarbons, which may be mixed with organic solvents, or aqueous suspensions pressurized with inert gases or gaseous hydrocarbons.

The amount of compound to be applied to the loci of insects and mites is not critical and can readily be determined by those skilled in the art in view of the examples provided. In general, concentrations of from about 10 ppm to about 5,000 ppm of the Formula 2 compound are expected to provide good control. With many of the compounds, concentrations of from about 100 to about 1,000 ppm will suffice. For field crops, such as soybeans and cotton, a suitable application rate for the compounds is about 0.01 to about 1 kg/ha, typically applied in a 5 to 50 gal/A of spray formulation.

The locus to which a Formula 2 compound is applied can be any locus inhabited by an insect or mite, for example, vegetable crops, fruit and nut trees, grape vines and ornamental plants. Because of the unique ability of mite eggs to resist toxicant action, repeated applications may be desirable to control newly emerged larvae, as is true of other known acaricides.

Ectoparasiticide Activity

The Formula 2 compounds are also active against members of the insect order Diptera. Tables XI and XII summarize the in viro studies of the Formula 2 compounds against blowfly larvae and adult stable fly at 48 hours.

TABLE XI

Activity Against Blowfly Larvae

| Compound | Activity rate (ppm) | % mortality |
|---|---|---|
| A83543K | 2.5 | 40 |
| A83543P | 10.0 | 10 |
| A83543W | 10.0 | 0 |
| A83543Y | 10.0 | 100 |

TABLE XII

Activity Against Adult Stable fly

| Compound | Activity rate (ppm) | % mortality |
|---|---|---|
| A83543K | 2.5 | 90 |
| A83543O | 5 | 100 |
| A83543P | 10 | 90 |
| A83543W | 10 | 40 |
| A83543Y | 10 | 90 |

Ectoparasiticial Methods

The ectoparasiticidal method of this invention is carried out by administering a Formula 2 compound to host animals to control insect and Acarina parasites. Administration to the animal may be by the dermal, oral, or parenteral routes.

Parasitic insects and Acarina include species that are bloodsucking as well as flesh eating and are parasitic during all of their life cycle or only part of their life cycle, such as only the larval or only the adult stage. Representative species include the following:

| | |
|---|---|
| horse fly | Tabanus spp. |
| stable fly | Stomoxys calcitrans |
| black fly | Simulium spp. |
| horse sucking louse | Haematopinus asini |
| mange mite | Sarcoptes scabiei |
| scab mite | Psoroptes equi |
| horn fly | Haematobia irritans |
| cattle biting louse | Bovicola bovis |
| shortnosed cattle louse | Haematopinus eurysternus |
| longnosed cattle louse | Linognathus vituli |
| tsetse fly | Glossina spp. |
| cattle follicle mite | Demodex bovis |
| cattle tick | Boophilus microplus and B. decoloratus |
| Gulf Coast tick | Amblyomma maculatum |
| Lone Star tick | Amblyomma americanum |
| ear tick | Otobius megnini |
| Rocky Mountain wood tick | Dermacentor andersoni |
| screw-worm fly | Cochliomyia hominivorax |
| assassin bug | Reduvius spp. |
| mosquito | Culiseta inornata |
| brown ear tick | Rhipicephalus appendiculatus |
| African red tick | Rhipicephalus evertsi |
| bont tick | Amblyomma sp. |
| bont legged tick | Hyalomma sp. |
| hog louse | Haematopinus suis |
| chigoe | Tunga penetrans |
| body louse | Haematopinus ovillus |
| foot louse | Linognathus pedalis |
| sheep ked | Melophagus ovinus |
| sheep scab mite | Psoroptes ovis |
| greenbottle fly | Phaenicia sericata |
| black blow fly | Phormia regina |
| secondary screw-worm | Cochliomyia macellaria |
| sheep blow fly | Phaenicia cuprina |
| bed bug | Cimex lectularius |
| Southern chicken flea | Echidnophaga gallinacea |
| fowl tick | Argas persicus |
| chicken mite | Dermanyssus gallinae |
| scalyleg mite | Knemidokoptes mutans |
| depluming mite | Knemidokoptes gallinae |
| dog follicle mite | Demodex canis |
| dog flea | Ctenocephalis canis |
| American dog tick | Dermacentor variabilis |
| brown dog tick | Rhipicephalus sanguineus |

The method of the invention may be used to protect economic and companion animals from ectoparasites. For example, the compound may beneficially be administered to horses, cattle, sheep, pigs, goats, dogs, cats and the like, as well as to exotic animals such as camels, llamas, deer and other species which are commonly referred to as wild animals. The compound may also beneficially be administered to poultry and other birds, such as turkeys, chickens, ducks and the like. Preferably, the method is applied to economic animals, and most preferably to cattle and sheep.

Ectoparasiticidal Compositions

This invention also relates to compositions for controlling a population of insect ectoparasites which consume blood of a host animal. These compositions may be used to protect economic, companion, and wild animals from ectoparasites. The compositions may also beneficially be administered to poultry and other birds.

Preferably, the method is applied or the compositions are used to protect economic animals, and most preferably to cattle and sheep. The rate, timing and manner of effective application will vary widely with the identity of the parasite, the degree or parasital attack and other factors. Applications can be made periodically over the entire life span of the host, or for only peak season of parasitic attack. In general ectoparasite control is obtained with topical application of liquid formulations containing from about 0.0005 to about 95% of the Formula 2 compound, preferably up to 5%, and most preferably up to 1% of a Formula 2 compound. Effective parasite control is achieved at an administration rate from about 5 to about 100 mg/kg.

The Formula 2 compounds are applied to host animals by conventional veterinary practices. Usually the compounds are formulated into ectoparasiticidal compositions which comprise a Formula 2 compound and a physiologically-acceptable carrier. For example, liquid compositions may be simply sprayed on the animals for which ectoparasiticidal control is desired. The animals may also treat themselves by such devices as back rubbers which may contain the Formula 2 compound and a cloth, for example, which the animal may walk against in contact. Dip tanks are also employed to administer the active agent to the host animal.

Oral administration may be performed by mixing the compound in the animals' feed or drinking water, or by administering dosage forms such as tablets, capsules, boluses or implants. Percutaneous administration is conveniently accomplished by subcutaneous, intraperitoneal, and intravenous injection of an injectible formulation.

The Formula 2 compounds can be formulated for oral administration in the usual forms, such as drenches, tablets or capsules. Such compositions, of course, require orally-acceptable inert carriers. The compounds can also be formulated as an injectible solution or suspension, for subcutaneous, dermal, intraruminal, intraperitoneal, intramuscular, or intravenous injection. In some applications the compounds are conveniently formulated as one component of a standard animal feed. In this embodiment it is usual to formulate the present compound first as a premix in which the compound is dispersed in a liquid or particulate solid carrier. The premix can contain from about 2 to about 250 g of Formula 2 compound per pound of mix. The premix is in turn formulated into the ultimate feed by conventional mixing.

Because ectoparasitic attack generally takes place during a substantial portion of the host animal's life span, it is preferred to administer Formula 2 compounds in a form to provide sustained release over a period of time. Conventional procedures include the use of a matrix which physically inhibits dissolution, where the matrix is a waxy semi-solid, such as the vegetable waxes, or a high molecular weight polyethylene glycol. A good way to administer the compounds is by means of a sustained-action bolus, such as those of Laby, U.S. Pat. No. 4,251,506 and Simpson, British Patent No. 2,059,767. For such a bolus the compound would be encapsulated in a polymeric matrix such as that of Nevin, U.S. Pat. No. 4,273,920. Sustained release of the compounds of the present invention can also be achieved by the use of an implant such as from a silicone-containing rubber.

In order to illustrate more fully the operation of this invention, the following examples are provided:

EXAMPLE 1

A83543 Assay Method

The following analytical high performance liquid chromatography (HPLC) method is useful for monitoring a fermentation for the production of A83543K, A83543O, A83543P, A83543U, A83543V, A83543W, A83543Y and other A83543 components:

A sample of the whole broth is diluted with three volumes of acetonitrile to extract the factors from the mycelia. The resulting solution is then filtered through a 0.45 micron polytetrafluorine (PTFE) filter to remove particulate matter prior to injection into the HPLC assay system. A solution of purified A83543A at a concentration of 100 mg/ml in methanol is used as an external standard for the assay and peak areas of all A83543 components are related back to this calibration standard to determine concentrations of individual components.

HPLC System:

Column Support: YMC-PACK 4.6×100-mm ID column, 5 μ spherical, 120 Å (YMC Inc., Morris Plains, N.J.)

Mobile Phase: $CH_3CN/MeOH/H_2O$ (3:3:2) containing 0.05% ammonium acetate

Flow Rate: 2 ml/min

Detection: UV at 250 nm

| Retention Times: | A83543A | 15.52 min |
|---|---|---|
| | A83543K | 8.10 min |
| | A83543O | 11.40 min |
| | A83543P | 6.40 min |
| | A83543U | 5.22 min |
| | A83543V | 7.05 min |
| | A83543W | 8.47 min |
| | A83543Y | 6.12 min |

EXAMPLE 2

Preparation of A83543K and A83543O with Culture NRRL 18538 (A83543.4)

A. Shake-flask Fermentation

The culture S. spinosa NRRL 18538, either as a lyophilized pellet or as a suspension maintained in liquid nitrogen, was used to inoculate a vegetative medium having the following composition:

| Vegetative Medium 1 | |
|---|---|
| Ingredient | Amount (g) |
| Enzyme-hydrolyzed casein* | 30 |
| Yeast extract | 3 |
| $MgSO_4.7H_2O$ | 2 |
| Glucose | 10 |
| Deionized water | q.s. 1-L |
| pH 6.2, adjust to pH 6.5 with NaOH | |

*NZ Amine A, Sheffield Products, Norwich, NY.

Slants or plates can be prepared by adding 2.5% agar to the vegetative medium. The inoculated slant is incubated at 30° C. for about 10 to about 14 days. The mature slant culture is scraped with a sterile tool to loosen the spores and to remove and macerate the mycelial mat. About one-fourth of the loosened spores and culture growth thus obtained is used to inoculate 50 ml of a first-stage vegetative medium. Alternatively, the first-stage medium may be inoculated from a liquid nitrogen ampoule.

When culture is maintained in liquid nitrogen, ampoules are prepared using equal volumes of vegetative culture (48–72 hours incubation, 30° C.) and suspending medium. The suspending medium contains lactose (100 g), glycerol (200 ml), and deionized water (q.s. to 1-L).

A liquid nitrogen ampoule is used to inoculate 50 ml of vegetative medium in 250-ml Erlenmeyer flasks. The cultures are incubated at 30° C. for 48 hours on a shaker orbiting in a two-inch (5.08 cm) circle at 250 rpm.

The incubated culture (5% v/v inoculum) is used to inoculate 30 ml of a production medium in a 250-ml wide-mouth Erlenmeyer flask. The medium composition was as follows:

| Production Medium | |
|---|---|
| Ingredient | Amount (g) |
| Glucose | 80 |
| Peptonized milk* | 20 |
| Cottonseed flour** | 30 |
| Corn steep liquor | 10 |
| $CaCO_3$ (tech. grade) | 5 |
| Methyl oleate | 30*** |
| Tap water | q.s. to 1-L |

*Peptonized Milk Nutrient, Sheffield Products, Norwich, NY
** Proflo, Traders Protein, Memphis, TN
***The amount of methyl oleate was 30 ml The inoculated production medium is incubated in 250-ml wide-mouth Erlenmeyer flasks at 30° C. for 7 days on a shaker orbiting in a two-inch circle at 250 rpm. Sinefungin was added at a final concentration of about 100 μg/ml, at 72 hours after inoculation.

B. Stirred Reactor Fermentation

In order to provide a larger volume of inoculum, 10 ml of incubated first stage medium, prepared as described in Example 2, Section A, is used to inoculate 400 ml of a second-stage vegetative medium having the same composition as that of the first-stage medium. This second-stage vegetative medium is incubated in a 2-L wide-mouth Erlenmeyer flask for about 48 hours at 30° C. on a shaker orbiting in a two-inch circle at 250 rpm.

Incubated second-stage vegetative medium (2-L) thus prepared is used to inoculate 115 liters of sterile production medium, prepared as described in Example 2, Section A. Sinefungin, as a filtered methanolic solution, was added at 66 hours to a final concentration of 100 μg/ml.

The inoculated production medium was allowed to ferment in a 165-L stirred bioreactor for 7 days at a temperature of 30° C. The air-flow and agitator speed in the stirred vessel are computer controlled to maintain a dissolved oxygen level at about 80% of air saturation.

EXAMPLE 3

Preparation of A83543K, A83543O and A83543Y with Culture NRRL 18743 (A83543.8)

A. Shake-flask Fermentation

The culture S. spinosa NRRL 18743, either as a lyophilized pellet or as a suspension maintained in liquid nitrogen, was used to inoculate a vegetative medium having the following composition:

| Vegetative Medium 2 | |
|---|---|
| Ingredient | Amount (g) |
| Trypticase soy broth* | 30 |
| Yeast extract | 3 |
| $MgSO_4.7H_2O$ | 2 |
| Glucose | 5 |
| Maltose | 4 |

-continued

Vegetative Medium 2

| Ingredient | Amount (g) |
| --- | --- |
| Deionized water<br>autoclave 30 min at 120° C. | q.s. 1-L |

*Baltimore Biological Laboratories, Cockeysville, MD

Slants or plates can be prepared by adding 2.5% agar to the vegetative medium. The inoculated slant is incubated at 30° C. for about 10 to about 14 days. The mature slant culture is scraped with a sterile tool to loosen the spores and remove and macerate the mycelial mat. About one-fourth of the loosened spores and culture growth thus obtained is used to inoculate 50 ml of a first-stage vegetative medium. Alternatively, the first-stage medium may be inoculated from a liquid nitrogen ampoule.

Liquid-nitrogen-stock inoculum was prepared by homogenizing a vegetative culture, diluting 1:1 (volume:volume) with a sterile suspending agent of glycerol:lactose:water (2:1:7), and dispensing into sterile tubes (1.5 ml/tube). The diluted inoculum was then stored over liquid nitrogen in appropriate storage containers and used as a working stock inoculum for the cultivation of shake-flask cultures and fermenter seed inoculum.

A liquid nitrogen ampoule was quick thawed and 0.5 ml was used to inoculate 50 ml of vegetative medium in 250-ml wide-mouth Erlenmeyer flasks. The cultures are incubated at 32° C. for 48 hours on a shaker orbiting in a two-inch (5.08 cm) circle at 250 rpm.

The incubated culture (5% v/v inoculum) is used to inoculate 25 ml of a production medium having the following composition:

Production Medium

| Ingredient | Amount (g) |
| --- | --- |
| Glucose | 80 |
| Peptonized milk* | 20 |
| Cottonseed flour** | 30 |
| Corn steep liquor | 10 |
| CaCO$_3$ (tech. grade) | 5 |
| Methyl oleate | 30 |
| Tap water | q.s. to 1-L |

*Peptonized Milk Nutrient, Sheffield Products, Norwich, NY
**Proflo, Traders Protein, Memphis TN The inoculated production medium is incubated in 250-ml wide-mouth Erlenmeyer flasks at 30° C. for 7 days on a shaker orbiting in a two-inch circle at 250 rpm.

B. Stirred Reactor Fermentation

In order to provide a larger volume of inoculum, 10 ml of incubated first stage medium, prepared as described in Example 3, Section A, is used to inoculate 400 ml of a second-stage vegetative medium having the same composition as that of the first-stage medium. This second-stage vegetative medium is incubated in a 2-L wide-mouth Erlenmeyer flask for about 48 hours at 32° C. on a shaker orbiting in a two-inch circle at 250 rpm.

Incubated second-stage vegetative medium (2-L) thus prepared is used to inoculate 115 liters of sterile production medium, prepared as described in Example 3, Section A.

The inoculated production medium is allowed to ferment in a 165-L stirred bioreactor for 7 days at a temperature of 30° C. The air-flow and agitator speed in the stirred vessel are computer controlled to maintain a dissolved oxygen level at or above 80% of air saturation.

EXAMPLE 4

Isolation of A83543P and A83543W from NRRL 18719 (A83543.6) fermented in the presence of sinefungin Fermentation broth (190-L stirred fermenter), prepared substantially as described in Example 2B (with the exception that strain A83543.6 was used), was refrigerated two days prior to processing. Acetone (190-L) was added to the whole broth after adjusting the pH to 3.0 with 5N HCl. The resulting mixture was filtered through a ceramic filter to give filtrate (335-L) which was held over the weekend under refrigeration. The broth/acetone filtrate was adjusted to pH 10 with 5N NaOH and refiltered through the ceramic filter prior to loading onto a steel column (10-L; 10 cm×122 cm) containing HP-20ss resin (Mitsubishi Chemical Industries, Ltd., Japan) at a flow rate of 1-L/minute. The column was washed with CH$_3$CN - CH$_3$OH - 0.1% aq. NH$_4$OAc (adjusted to pH 8.1 with NH$_4$OH) (25:25:50; 20-L), then eluted with CH$_3$CN - CH$_3$OH - 0.1% aq. NH$_4$OAc (adjusted pH 8.1 with NH$_4$OH) (95:95:10; 40-L), collecting 2-L fractions. Fractions 3–9 were concentrated to dryness, redissolved in CH$_3$OH (100 ml), reconcentrated, then precipitated into CH$_3$CN (1-L). The resulting precipitate was removed by filtration and discarded; the filtrate was concentrated to dryness. The resulting residue was redissolved in dichloromethane (25 ml) and applied to a column (7.5 cm×50 cm) of silica gel (EM grade 62, 60 - 200 mesh) equilibrated in acetonitrile. The column was eluted with CH$_3$CN (4-L), then CH$_3$CN - CH$_3$OH (9:1; 5-L), followed by CH$_3$OH (1-L), collecting 1-L fractions. Pool 1 (fractions 3–4) contained A83543 components J and L; pool 3 (fractions 7–10), components M and N. Pool 2 (fractions 5–6), containing new components P and W, was concentrated to dryness. The resulting residue was dissolved in CH$_3$OH (10 ml) and applied to a preparative reverse phase HPLC column (Rainin Dynamax-60 Å 8 µm C18, 41.4 mm ID×25 cm with 41.4 mm×5 cm guard module) equilibrated in H$_2$O - CH$_3$OH - CH$_3$CN; (30:35:35, containing 0.1% NH$_4$OAc). The column was eluted at a flow rate of 40 ml/minute with a gradient mixed from solvent "A" H$_2$O - CH$_3$OH - CH$_3$CN (30:35:35, containing 0.1% NH$_4$OAc) and solvent "B" H$_2$O - CH$_3$OH - CH$_3$CN; (10:45:45, containing 0.1% NH$_4$OAc). The pumping system was programmed to generate a linear gradient from 25 to 75% B in 60 minutes. Progress of the separation was monitored with a variable wavelength UV detector tuned to 250 nm. The major peak was collected in 6×3 minute fractions. Fractions 1–2, containing new component P, were concentrated to 40 ml, then desalted on the same HPLC column equilibrated in H$_2$O - CH$_3$OH - CH$_3$CN (30:35:35) by eluting with a 60 minute linear gradient from H$_2$O - CH$_3$OH - CH$_3$CN (30:35:35) to H$_2$O - CH$_3$OH - CH$_3$CN (10:45:45). The UV absorbing peak (minus the first 2 minutes eluted) was collected and concentrated to dryness. The resulting residue was dissolved in t-BuOH (10 ml) and lyophilized to give pure component P (479 mg). Pooled fractions 3–4 from above, containing a mixture of component P and W, were concentrated to 20 ml and applied to a preparative reverse phase HPLC column (Rainin Dynamax-60 Å 8 µm C18, 21.4 mm ID×25 cm with 21.4 mm×5 cm guard module), equilibrated in H$_2$O - CH$_3$OH - CH$_3$CN (30:35:35) containing 0.1% NH$_4$OAc, and eluted at a flow rate of 10 ml/minute with a gradient mixed from solvent "A" H$_2$O - CH$_3$OH - CH$_3$CN; (30:35:35, containing 0.1% NH$_4$OAc) and solvent "B" H$_2$O - CH$_3$OH - CH$_3$CN; (10:45:45, containing 0.1% NH$_4$OAc). The pumping system was programmed to generate a linear gradient from 25 to 75% B in 60 minutes. Two major UV absorbing peaks (component P, followed by component W) were collected. The component W containing pool was concentrated to a small volume, then desalted on the same HPLC column equilibrated in $H_2O$ - $CH_3OH$ - $CH_3CN$ (30:35:35). Component W was eluted with a 60 minute linear gradient from $H_2O$ - $CH_3OH$ - $CH_3CN$ (30:35:35) to $H_2O$ - $CH_3OH$ - $CH_3CN$ (10:45:45) at a flow rate of 10 ml/minute, collecting UV absorbing peak into 10×3 minute fractions. Pooled fractions 2–7 were concentrated to residue, dissolved in t-BuOH, and lyophilized to give pure component W (82 mg). The component P-containing UV absorbing peak from above was desalted in like manner to give additional pure component P (132 mg).

EXAMPLE 5

Isolation of A83543U and A83543V from strain NRRL 18823 (A83543.9) fermented in the presence of sinefungin Fermentation broth (500 ml; 30×250 ml shake flasks) prepared substantially as described in Example 2A (except strain A83543.9 was used), was extracted with methanol (1.3-L) with stirring for one hour, then filtered using a filter aid (3% Hyflo) to give methanolic filtrate (1.5-L). The biomass was reextracted with methanol (700 ml) and filtered. The two methanolic extracts were combined and an equal volume of water added. HP-20 resin (75 ml) was added and stirred for 2 hours, after which the slurry was poured into a glass chromatography column. The effluent (5-L) was discarded, as was a $CH_3OH$ - $H_2O$ (1:1) wash (500 ml) of the column. The column was then eluted with acetone (250 ml). The acetone eluate was combined with that obtained from a similar extraction and chromatography of whole broth (500 ml; 40×250 ml shake flasks) and concentrated to dryness. The resulting residue was dissolved in dichloromethane (10 ml) and applied to a column (2.5 cm×25 cm) of silica gel (EM grade 62, 60 - 200 mesh) equilibrated in acetonitrile. The column was washed with acetonitrile, then eluted with a linear gradient from acetonitrile to acetonitrile - methanol (4:1), collecting 25 ml fractions. Fractions 34–43, containing new A83543 components U and V were pooled (200 ml), and concentrated to dryness. The residue was dissolved in methanol (2 ml) and applied to a preparetive reverse phase HPLC column (Rainin Dynamax-60 Å 8 μm C18, 21.4 mm ID×25 cm with 21.4 mm×5 cm guard module) equilibrated in $H_2O$ - $CH_3OH$ - $CH_3CN$ (30:35:35) containing 0.1% $NH_4OAc$. The column was eluted with a 60 minute linear gradient from $H_2O$ - $CH_3OH$ - $CH_3CN$ (30:35:35) containing 0.1% $NH_4OAc$ to $H_2O$ - $CH_3OH$ - $CH_3CN$ (10:45:45) containing 0.1% $NH_4OAc$ at a flow rate of 10 ml/minute. The major peaks (UV monitored at 250 nm), containing new components U and V, were collected before residual components H and Q. The pool containing component U was desalted on the same HPLC column equilibrated in $H_2O$ - $CH_3OH$ - $CH_3CN$ (30:35:35) by eluting with a linear gradient from $H_2O$ - $CH_3OH$ - $CH_3CN$ (30:35:35) to $H_2O$ - $CH_3OH$ - $CH_3CN$ (10:45:45). Component U was eluted in 2 minute fractions (10). Fractions 2–8 were pooled, then concentrated to dryness. The residue was dissolved in t-BuOH (5 ml) and lyophilized to give pure component U (71 mg). The component V-containing pool was desalted and lyophilized by the same procedure to give pure component V (7 mg).

EXAMPLE 6

Isolation of A83543K and A83543O from NRRL 18538 (A83543.4) fermented in the presence of sinefungin Fermentation broth (210-L stirred fermenter) was prepared substantially as described in Example 2B. Acetone was added to the whole broth and the pH was adjusted to 8.0. The resulting mixture was filtered through a ceramic filter to give filtrate (370-L). The broth/acetone filtrate was loaded onto a steel column (10-L, 10 cm×122 cm) containing HP-20ss resin (Mitsubishi Chemical Industries, Ltd., Japan) at a flow rate of 1-L/minute, collecting the effluent in a single pool. The column was eluted at a flow rate of 1-L/minute with a gradient mixed from solvent "A" (0.1% $NH_4OAc$) and solvent "B" ($CH_3OH$ - $CH_3CN$; 1:1). The pumping system was programmed to deliver 50% B for 2 minutes, followed by a linear gradient from 50–80% B (45 minutes), followed by a linear gradient from 80–90% B (33 minutes), collecting 20×4 L fractions. Fractions 13–17, containing components K and O were pooled. The column effluent (see above) was adjusted to pH 9.5 with 5N NaOH and reapplied to the HP-20ss column. The pumping system was programmed to deliver 50% B for 1 minute, a linear gradient from 50–75% B (30 minutes), a linear gradient from 75–85% B (45 minutes), a linear gradient from 85–88% B (15.4 minutes), and a linear gradient from 88–100% B (20 minutes), at a flow rate of 1-L/minute, collecting 22×4 L fractions. Fractions 7–17 were pooled and combined with the pool (fractions 13–17 from the first HP-20ss chromatography (see above). The combined pools were concentrated to 4-L, then further concentrated to dryness, redissolved in $CH_3OH$ (100 ml), then precipitated into $CH_3CN$ (3-L). The resulting precipitate was removed by filtration, washed with $CH_3CN$, and discarded; the filtrate was concentrated to dryness. The resulting residue was redissolved in dichloromethane (50 ml) and applied to a column (6 cm×24 cm) of silica gel (EM grade 62, 60 - 200 mesh) equilibrated in acetonitrile. The column was eluted with $CH_3CN$ (4-L), then $CH_3CN$ - $CH_3OH$ (9:1; 10-L), taking 10×250 ml fractions, followed by 7×1 L fractions. Fractions 6–15, containing components K and O, were concentrated to dryness. The resulting residue was dissolved in $CH_3OH$ (100 ml) and applied (in 20 runs) to a preparative reverse phase HPLC column (Rainin Dynamax-60 Å 8 μm C18, 41.4 mm ID×25 cm with 41.4 mm×5 cm guard module) equilibrated in $H_2O$ - $CH_3OH$ - $CH_3CN$; (50:175:175, containing 0.1% $NH_4OAc$). The column was eluted at a flow rate of 40 ml/minute. Progress of the separation was monitored with a variable wavelength UV detector tuned to 250 nm. UV absorbing peaks (from the 20 chromatographic runs) were collected in 7 pools. The two largest peaks corresponded to components K and O. Pool 3 (6-L), contained component K (98% pure). Pool 4 (8-L), containing components O and K, was concentrated to 200 ml and rechromatographed (in 4 runs) under the same conditions, collecting the two peaks as two pools. Pool 1 (3-L) contained component K (98% pure). Pool 2 (5-L), contained component O (95%) and component K (5%). Pool 2 was concentrated to 100 ml and desalted by chromatography on the same HPLC column (in 3 runs), eluting with a 60 minute linear gradient from $H_2O$ - $CH_3OH$ - $CH_3CN$ (30:35:35) to $H_2O$ - $CH_3OH$ - $CH_3CN$ (10:45:45). The UV absorbing eluate was collected in 10×3 minute fractions. Fractions containing >98% pure component O were pooled, concentrated to dryness, and lyophilized from t-BuOH to give component O (2.5 g; >98% pure). Component K containing pools from the first preparative HPLC separation (pool 3, 6-L) and the repurification of component O (pool 1, 3-L) were combined, concentrated to 200 ml, and desalted in the same manner as component O. Fractions containing >98% pure component K were pooled, concentrated to dryness, and lyophilized from t-BuOH to give component K (11.1 g; >99% pure).

EXAMPLE 7

Isolation of A83543K, A83543O, and A83543Y from strain NRRL 18743 (A83543.8)

Fermentation broth (260-L) was prepared as substantially described in Example 3B. Acetone (260-L) was added to the whole broth after adjusting the pH to 3.0 with 5N HCl. The resulting mixture was filtered through a ceramic filter to give filtrate (480-L) which was held over the weekend under refrigeration. The broth/acetone filtrate was adjusted to pH 12 with 25% NaOH and refiltered twice through the ceramic filter prior to loading onto a steel column (10-L, 10 cm×122 cm) containing HP-20ss resin (Mitsubishi Chemical Industries, Ltd., Japan) at a flow rate of 0.5-L/minute. The column was washed with $CH_3CN$ - $CH_3OH$ - 0.1% aq. $NH_4OAc$ (adjusted to pH 8.1 with $NH_4OH$) (25:25:50; 20-L). New components K, O and Y were eluted with $CH_3CN$ - $CH_3OH$ - 0.1% aq. $NH_4OAc$ (adjusted to pH 8.1 with $NH_4OH$) (95:95:10; 30-L) at a flow rate of 1-L/minute. The eluate (30-L) was concentrated, redissolved in $CH_3OH$, reconcentrated to dryness, redissolved in $CH_3OH$ (100 ml), then precipitated into $CH_3CN$ (2-L). The resulting precipitate was removed by filtration, washed with $CH_3CN$, and discarded; the combined filtrate and wash (3-L) was concentrated to dryness. The resulting residue was redissolved in dichloromethane (50 ml) and applied to a column (7.5 cm×50 cm) of silica gel (EM grade 62, 60 - 200 mesh) equilibrated in acetonitrile. The column was eluted with $CH_3CN$ (10-L), then $CH_3CN$ - $CH_3OH$ (9:1; 20-L), followed by $CH_3CN$ - $CH_3OH$ (8:2; 10-L), collecting 1-L fractions. Fractions 11–30 were pooled and concentrated to dryness. The resulting residue was dissolved in $CH_3OH$ (50 ml) and applied (in 10 runs) to a preparative reverse phase HPLC column (Rainin Dynamax-60 Å 8 µm C18, 41.4 mm ID×25 cm with 41.4 mm×5 cm guard module) equilibrated in $H_2O$ - $CH_3OH$ - $CH_3CN$; (50:175:175, containing 0.1% $NH_4OAc$). The column was eluted at a flow rate of 40 ml/minute with a 60 minute linear gradient from $H_2O$ - $CH_3OH$ - $CH_3CN$; (50:175:175, containing 0.1% $NH_4OAc$) to $H_2O$ - $CH_3OH$ - $CH_3CN$; (10:45:45, containing 0.1% $NH_4OAc$). Progress of the separation was monitored with a variable wavelength UV detector tuned to 250 nm. The first three peaks collected (10 runs pooled) corresponded to the elution of minor component Y (pool 1, 1-L), component K (pool 2, 8-L) and component O (pool 3, 4-L). Pool 2 was concentrated to a small volume, then desalted by rechromatographing on the same column, eluting without buffer. The effluent corresponding to the UV absorption peak was concentrated to dryness, dissolved in t-BuOH, and lyophilized to give pure component K (7.3 g). Pool 3 was desalted and lyophilized in like manner to give pure component O (1.4 g). Pool 1 was desalted by similar chromatography (Rainin Dynamax-60 Å 8 µm C18 column, 21.4 mm ID×25 cm with 21.4 mm×5 cm guard module) and lyophilized in like manner to give pure component Y (46 mg).

EXAMPLE 8

A83543K pseudoaglycone

A sample of A83543K (100 mg) was dissolved in 2N sulfuric acid (10 ml). This solution was heated at about 80° C. for 1.25 hours, and the resulting mixture was allowed to cool to room temperature. The precipitate was collected by filtration, washed with cold deionized water, and dried to give 59 mg of A83543K pseudoaglycone.

Elemental Analysis

MS (FD): m/z 576 (100%)

IR ($CHCl_3$): 2936.0, 1714.9, 1659.0 $cm^{-1}$

UV (EtOH): $\lambda_{max}$ 243 nm (Qualitative)

EXAMPLE 9

A83543O Pseudoaglycone

A sample of A83543O (500 mg) was suspended in deionized water (40 ml) and a sufficient volume of 1N $H_2SO_4$ was added to cause complete dissolution (approximately 0.25 ml). The resulting solution was heated at about 80° C. for 3 hours, and then allowed to cool to room temperature. The precipitate was collected by filtration, washed with cold deionized water, and dried. The filtrate was saturated with NaCl and extracted with methylene chloride. The methylene chloride extracts were combined, extracted with brine, dried ($K_2CO_3$), and evaporated to dryness. The residue was combined with the precipitate to give 348 mg of crude product.

The crude product was purified by flash chromatography (Silica gel 60, 230–400 mesh), eluting with a mixture of ethyl acetate and hexane (7:3). The fractions containing the desired compound were evaporated to dryness to give 146.5 mg of A83543O pseudoaglycone.

Elemental Analysis

MS (FD): m/z 590 (100%), 591 (70%, M+), 592 (20%, M+H), 593 (5&, M+2)

IR ($CHCl_3$): 3014.2, 2932.2, 1714.9, 1659.0 $cm^{-1}$

UV (EtOH): $\lambda_{max}$ 242 nm ($\epsilon$ 9,185)

EXAMPLE 10

N-demethyl-A83543K

A83543K (101.5 mg, 0.14 mmol) and sodium acetate trihydrate (142.4 mg, 1.05 mmol) were added to a mixture of methanol and pH 9 buffer solution (Fisher Scientific, Lexington, Mass.). The resulting suspension was heated to about 47° C., and then iodine (47.7 mg, 0.19 mmol) was added in one portion. After 2½ hours at 47° C., the reaction was allowed to cool to room temperature. After stirring an additional 3 hours at room temperature, the reaction solution was added to a 5% sodium thiosulfate solution. The resulting colorless aqueous mixture was extracted with diethyl ether. The aqueous layer was then saturated with NaCl and extracted with methylene chloride. The methylene chloride extracts were combined with the diethyl ether extracts, washed with brine, and dried over $K_2CO_3$. The dried solution was then evaporated to dryness in vacuo to give 79.3 mg of N-demethyl-A83543K as a white glass (81% yield).

MS (FD): m/z 703 (100%, M+), 704 (57%, M+H), 705 (19%, M+2)

Elemental Analysis ($C_{39}H_{61}NO_{10}$) Calc.: C, 66.55; H, 8.73; N, 1.99; Found: C, 64.80; H, 8.67; N, 1.95

IR (KBr): 3462.7, 2934.1, 1721.7, 1660.9, 1457.4 $cm^{-1}$.

EXAMPLE 11 di-N-demethyl-A83543K

A solution of N-demethyl-A83543K (891 mg, 1.27 mmol) in MeOH (40 ml) was cooled to 3° C. Freshly prepared 1M NaOMe in methanol (6.3 ml, 6.3 mmol) and iodine (1.61 g, 6.3 mmol) were successively added to this solution. The reaction solution was kept at 3° C. for 5 hours, then added to a 5% sodium thiosulfate/dilute ammonium hydroxide solution. The resulting mixture was extracted with ethyl acetate. The combined ethyl acetate extracts were washed with brine and dried over $K_2CO_3$. The dried solution was evaporated to dryness in vacuo to give 770 mg of crude product.

The desired compound was partially purified by flash chromatography (Silica gel 60, 230–400 mesh, 2 in.×8 in.), eluting with a mixture of methylene chloride and methanol (93:7). The desired compound was further purified by reverse-phase HPLC (Waters Prep NOVA-Pak, ODS, 60 Å, 40 mm×300 mm), eluting with methanol/acetonitrile/0.25% ammonium acetate (40:40:20), giving 463.6 mg (53% yield) of di-N-demethyl-A83543K as a colorless glass.

Elemental analysis ($C_{38}H_{59}NO_{10}$) Calc.: C, 66.16; H, 8.62; N, 2.03; Found: C, 66.29; H, 8.63; N, 2.02, MS(FD): m/z 690 (100%, M+), 689 (70%), 691 (59%, M+H), 704 (20%)

UV (EtOH): $\lambda_{max}$ 244 nm ($\epsilon$ 10,328)

IR ($CHCl_3$): 3700, 3600, 3550-3350 (br), 3420, 2975, 1700, 1675, 1620 $cm^{-1}$.

What is claimed is:

1. A method of reducing a population of insect ectoparasites which consume blood of a host animal which comprises administering to the host animal an insect-inactivating amount of a compound of the following formula:

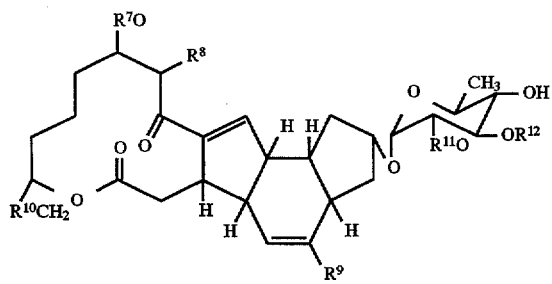

wherein $R^7$ is hydrogen or a group of formula

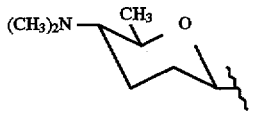
(a)

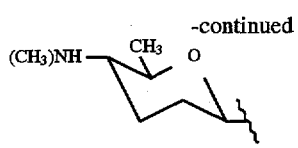
(b)

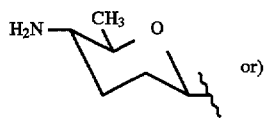
(c)

or)

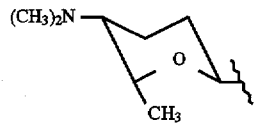
(d)

$R^8$, $R^9$, $R^{10}$, $R^{11}$, and $R^{12}$ are independently hydrogen or methyl, provided that $R^{11}$ and $R^{12}$ are not concurrently hydrogen; or an acid addition salt thereof when $R^7$ is other than hydrogen.

2. The method of claim 1 wherein $R^7$, $R^8$, $R^9$, $R^{10}$, $R^{11}$, and $R^{12}$ are for each component as follows:

| Component | $R^7$ | $R^8$ | $R^9$ | $R^{10}$ | $R^{11}$ | $R^{12}$ |
|---|---|---|---|---|---|---|
| K | (a) | $CH_3$ | H | $CH_3$ | $CH_3$ | $CH_3$ |
| O | (a) | $CH_3$ | $CH_3$ | $CH_3$ | $CH_3$ | $CH_3$ |
| P | (a) | $CH_3$ | H | $CH_3$ | $CH_3$ | H |
| U | (a) | $CH_3$ | H | $CH_3$ | H | $CH_3$ |
| V | (a) | $CH_3$ | $CH_3$ | $CH_3$ | H | $CH_3$ |
| W | (a) | $CH_3$ | $CH_3$ | $CH_3$ | $CH_3$ | H |
| Y | (a) | $CH_3$ | H | H | $CH_3$ | $CH_3$ |

* * * * *